(12) United States Patent
Taylor et al.

(10) Patent No.: US 9,320,428 B2
(45) Date of Patent: Apr. 26, 2016

(54) PROGRAMMABLE MULTISPECTRAL ILLUMINATION SYSTEM FOR SURGERY AND VISUALIZATION OF LIGHT-SENSITIVE TISSUES

(75) Inventors: Russell H. Taylor, Severna Park, MD (US); Seth D. Billings, Pellston, MD (US); Peter L. Gehlbach, Hunt Valley, MD (US); Gregory D. Hager, Baltimore, MD (US); James T. Handa, Baltimore, MD (US); Jin Ung Kang, Ellicott City, MD (US); Balazs Vagvolgyi, Baltimore, MD (US); Raphael Sznitman, Baltimore, MD (US); Zachary Pezzementi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 889 days.

(21) Appl. No.: 13/387,950

(22) PCT Filed: Aug. 5, 2010

(86) PCT No.: PCT/US2010/044596
§ 371 (c)(1),
(2), (4) Date: Jan. 30, 2012

(87) PCT Pub. No.: WO2011/017550
PCT Pub. Date: Feb. 10, 2011

(65) Prior Publication Data
US 2012/0130258 A1 May 24, 2012

Related U.S. Application Data

(60) Provisional application No. 61/231,519, filed on Aug. 5, 2009, provisional application No. 61/325,647, filed on Apr. 19, 2010.

(51) Int. Cl.
*A61B 6/00* (2006.01)
*A61B 3/13* (2006.01)
*A61B 3/18* (2006.01)

(52) U.S. Cl.
CPC .... *A61B 3/13* (2013.01); *A61B 3/18* (2013.01)

(58) Field of Classification Search
None
See application file for complete search history.

(56) References Cited

U.S. PATENT DOCUMENTS 5,042,939 A  8/1991  Zayek
5,299,053 A  3/1994  Kleinburg et al.
(Continued)

OTHER PUBLICATIONS

Banker et al., "Vision-threatening complications of surgery for full-thickness macular holes". Ophthalmology 104, 1442-1453 (1997).
(Continued)

*Primary Examiner* — James Kish
(74) *Attorney, Agent, or Firm* — Venable LLP; Henry J. Daley; Laura G. Remus

(57) ABSTRACT

An observation system for viewing light-sensitive tissue includes an illumination system configured to illuminate the light-sensitive tissue, an imaging system configured to image at least a portion of the light-sensitive tissue upon being illuminated by the illumination system, and an image display system in communication with the imaging system to display an image of the portion of the light-sensitive tissue. The illumination system is configured to illuminate the light-sensitive tissue with a reduced amount of light within a preselected wavelength range compared to multispectral illumination light, and the image of the portion of the light-sensitive tissue is compensated for the reduced amount of light within the preselected frequency range to approximate an image of the light-sensitive tissue under the multispectral illumination.

15 Claims, 14 Drawing Sheets

(56) References Cited

U.S. PATENT DOCUMENTS

| | | | | |
|---|---|---|---|---|
| 6,478,424 | B1* | 11/2002 | Grinvald et al. | 351/206 |
| 2005/0041207 | A1* | 2/2005 | Miller et al. | 351/200 |
| 2006/0268231 | A1* | 11/2006 | Gil et al. | 351/221 |
| 2008/0304011 | A1 | 12/2008 | Ng et al. | |

OTHER PUBLICATIONS

Blumenkranz, "The chick chorioallantoic membrane as a model tissue for surgical retinal research and simulation". Retina 24(3) (2004) 427-434.

Byrnes et al., "Photic maculopathy after extracapsular cataract surgery a prospective study". Ophthalmology 99, 731-738 (1992).

Chang et al., "Acceleration methods for total variation-based image de-noising". SIAM Journal of Applied Mathematics 25(3) (2003) 982994.

Chow, "Shedding Some Light on Current Endoillumination: Brighter Light can be Safe Light". Retinal Physician. Jan. 2005. Retrieved from http://www.retinalphysician.com/article.aspx?artiele=100050).

Fleming et al., "Cooperative robot assistant for retinal microsurgery". International Conference on Medical Image Computing and Computer Assisted Intervention 11(2) (2008) 543-550.

Ham et al., "Action spectrum for retinal injury from near-ultraviolet radiation in the aphakic monkey". Am J Ophthalmol 93 (1982) 299-306.

International Commission on Non-Ionizing Radiation Protection: Guidelines on limits of exposure to broad-band incoherent optical radiation (0.38 to 3). Health Phys. 73, 539-554 (1997).

Khwarg et al., "Incidence, risk factors, and morphology in operating microscope light retinopathy". American Journal of Ophthalmology 103, 255-263 (1987).

Lowe et al., "Distinctive image features from scale-invariant keypoints". International Journal of Computer Vision 20 (2003) 91-110).

Mallick et al., "Specularity removal in images and videos: A PDE approach". European Conference on Computer Vision (2006) 550-563.

McDonald et al., "Light-induced maculopathy from the operating micro-scope in extracapsular cataract extraction and intraocular lens implantation". Ophthalmology 90, 945-951 (1983).

Michels et al., "Macular pho-totoxicity caused by fiberoptic endoillumination during pars plana vitrectomy". American Journal of Ophthalmol. 114, 287-292 (1992).

Museum of Broadcast Communication: Encyclopedia of Television (online), 2012, http://www.museum.tv/archives/etv/c/htmlc/colorization/_colorization.htm.

Ohji et al., *Vitreoretinal Surgery*. "Chapter 7: New Instruments in Vitrectomy". Berlin Heidelberg: Springer, 2007.

Perkin Elmer Optoelectronics. ACULED® VHLTM Standard White, Monochromatic and Multi-Colored Four-Chip LED Products. 2008.

Poliner et al., "Retinal pigment epitheliopathy after macular hole surgery". Ophthalmology 99, 16711677 (1992).

Rother et al., "Seeing 3D objects in a single 2D image". International Conference on Computer Vision (2009).

Skora et al., "Unsupervised colorization of black and white cartoons". In: Int. Symp. NPAR, Annecy, pp. 121-127 (2004).

Stewart et al., "The dual-bootstrap iterative closest point algorithm with application to retinal image registration". Medical Imaging, IEEE Transactions on 22(11) (Nov. 2003) 1379-1394.

International Search Report and Written Opinion of PCT/US2010/044596.

Sznitman et al., *Active Multispectral Illumination and Image Fusion for Retinal Microsurgery*. The Johns Hopkins University. Information Processing in Computer Assisted Interventions (IPCAI) Conference, Geneva, Jun. 2010, the entire contents of which are incorporated herein by reference.

Sznitman et al., "Active background modeling: Actors on a stage". ICCV, Workshop on Visual Surveillance (2009) 1222-1228.

Van Den Biesen et al., "Endoillumination during vitrectomy and phototoxicity thresholds". British Journal of Ophthalmology 84, 1372-1375 (2000).

Wang et al., "A generalized kernel consensus based robust estimator". IEEE Transactions on Pattern Analysis and Machine Intelligence 32(1) (Jan. 2010) 178-184.

Yatziv et al., "Fast image and video colorization using chrominance blending". IEEE Transactions on Image Processing 15,1120-1129 (2006).

\* cited by examiner

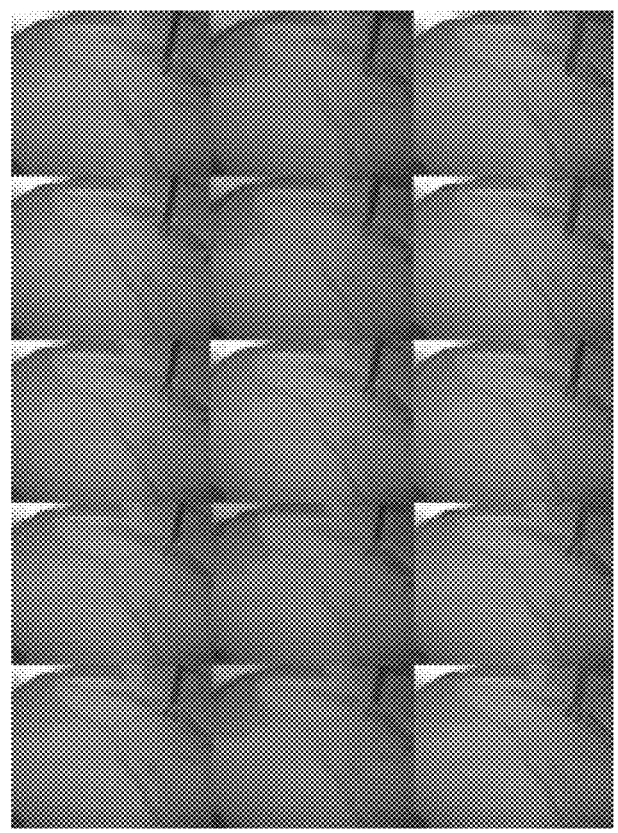
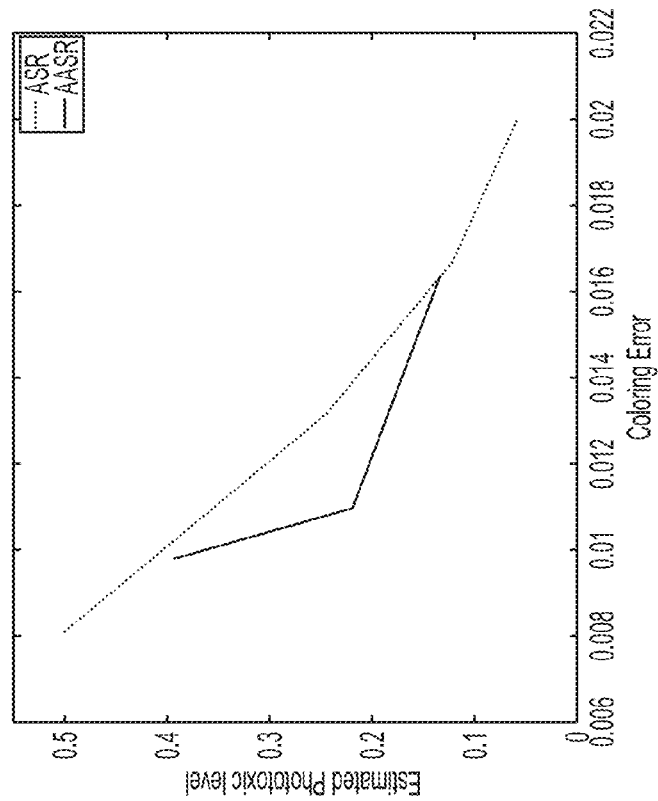
FIG. 11B
FIG. 11A

PROGRAMMABLE MULTISPECTRAL ILLUMINATION SYSTEM FOR SURGERY AND VISUALIZATION OF LIGHT-SENSITIVE TISSUES

CROSS-REFERENCE OF RELATED APPLICATION

This application claims priority to U.S. Provisional Application Nos. 61/231,519 filed Aug. 5, 2009 and 61/325,647 filed Apr. 19, 2010 the entire contents of which are hereby incorporated by reference, and is a national stage application under 35 U.S.C. §371 of PCT/US2010/044596 filed Aug. 5, 2010, the entire contents of which are incorporated herein by reference.

This invention was made with U.S. Government support of NSF Cooperative Agreement EEC9731478 and Grant No. 1 R01 EB 007969-01, awarded by the NIH. The U.S. Government has certain rights in this invention.

BACKGROUND

1. Field of Invention

The current invention relates to observation systems and methods of imaging light-sensitive tissue, and more particularly to observation systems and methods of imaging light-sensitive tissue with reduced phototoxicity.

2. Discussion of Related Art

Retinal microsurgery is one of the most demanding types of surgery. The difficulty stems from the microscopic dimensions of tissue planes and blood vessels in the eye, the delicate nature of the neurosensory retina and the poor recovery of retinal function after injury. Many micron-scale maneuvers are physically not possible for many retinal surgeons due to inability to visualize the tissue planes, tremor, or insufficient dexterity. To safely perform these maneuvers, microscopes are required to view the retina. A central issue for the surgeon is the compromise between adequate illumination of retinal structures, and the risk of iatrogenic phototoxicity either from the operating microscope or endoilluminators, which are fiber-optic light sources that are placed into the vitreous cavity to provide adequate illumination of the retina during delicate maneuvers.

Retinal phototoxicity from an operating microscope was first reported in 1983 in patients who had undergone cataract surgery with intraocular lens implantation (McDonald, H., Irvine, A.: Light-induced maculopathy from the operating micro-scope in extracapsular cataract extraction and intraocular lens implantation. Ophthalmology 90, 945-951 (1983)). Retinal phototoxicity is now a well recognized potential complication of any intraocular surgical procedure, and the frequency is reported to occur from 7% to 28% of patients undergoing cataract surgery (Khwarg, S., Linstone, F., Daniels, S., Isenberg, S., Hanscom, T., Geoghegan, M., Straatsma, B.: Incidence, risk factors, and morphology in operating microscope light retinopathy. American Journal of Ophthalmology 103, 255-263 (1987); Byrnes, G., Antoszyk, A., Mazur, D., Kao, T., Miller, S.: Photic maculopathy after extracapsular cataract surgery a prospective study. Ophthalmology 99, 731-738 (1992)). As a result, the International Commission on Non-Ionizing Radiation Protection (IC-NIRP) now provides safety guidelines for illumination of the fundus in both phakic and aphakic subjects (International Commission on Non-Ionizing Radiation Protection: Guidelines on limits of exposure to broad-band incoherent optical radiation (0.38 to 3). Health Phys. 73, 539-554 (1997)). Blue wavelength and ultraviolet light induce the greatest degree of retinal injury. In fact, in (van den Biesen, R., Berenschot, T., Verdaasdonk, R., van Weelden, H., van Norren, D.: Endoillumination during vitrectomy and phototoxicity thresholds. British Journal of Ophthalmology 84, 1372-1375 (2000)) it was found that commercially available light sources for endoillumination exceeded the ICNIRP guidelines for retinal damage by visible light within 3 minutes, and in 9 of 10 sources, the safe exposure time was exceeded in less than 1 minute. In vitrectomy for macular hole repair, up to 7% of the patients have been reported to have experienced visually significant phototoxicity (Poliner, L., Tornambe, P.: Retinal pigment epitheliopathy after macular hole surgery. Ophthalmology 99, 1671-1677 (1992); Michels, M., Lewis, H., Abrams, G., Han, D., Mieler, W., Neitz, J.: Macular pho-totoxicity caused by fiberoptic endoillumination during pars plana vitrectomy. American Journal of Ophthalmol. 114, 287-292 (1992); Banker, A., Freeman, W., Kim, J., Munguia, D., Azen, S.: Vision-threatening complications of surgery for full-thickness macular holes. Ophthalmology 104, 1442-1453 (1997)).

Phototoxicity can be either thermal or photochemical in nature from excessive ultraviolet (UV) or blue light toxicity. Ham et al. showed the action spectrum or relative risk of UV or blue light toxicity when the retina was exposed to various wavelengths of light (Ham, W. J., Mueller, H., Ru olo, J. J., Guerry, D., Guerry, R.: Action spectrum for retinal injury from near-ultraviolet radiation in the aphakic monkey. American Journal of Ophthalmology 93, 299-306 (1982)). The action spectrum was then used to create a relative risk of phototoxicity associated with a given wavelength of light.

The Aphakic Hazard Function describes the phototoxic potential of retinal light exposure within and near the visible spectrum. As seen from the curve in FIG. 1, retinal phototoxicity occurs primarily at short wavelengths, such as blue light. Red light has little to no phototoxic impact compared to blue light.

Current medical light sources attempt to limit phototoxicity by using filters to block wavelengths at the blue end of the visible spectrum. This approach has only limited usefulness, however, since blocking part of the visible spectrum hinders color rendition. Xenon is currently the illumination source of choice for retinal surgery. As shown on the Aphakic Hazard Function diagram (FIG. 1)(Ohji, Masahito and Tan θ, Yasuo. *Vitreo-retinal Surgery*. "Chapter 7: New Instruments in Vitrectomy". Berlin Heidelberg: Springer, 2007), a Xenon spectrum is fairly flat and has substantial coverage within the hazardous blue wavelength range. Thus, the industry standard light source for retinal surgery may be a significant health hazard for patients. The risk, while reduced, is still significant for intraocular surgery. Given the advancing age of the population and increasing prevalence of retinal diseases, there remains a need for further improvements aimed at reducing iatrogenic retinal phototoxicity.

SUMMARY

An observation system for viewing light-sensitive tissue according to an embodiment of the current invention includes an illumination system configured to illuminate the light-sensitive tissue, an imaging system configured to image at least a portion of the light-sensitive tissue upon being illuminated by the illumination system, and an image display system in communication with the imaging system to display an image of the portion of the light-sensitive tissue. The illumination system is configured to illuminate the light-sensitive tissue with a reduced amount of light within a preselected wavelength range compared to multispectral illumination light, and the image of the portion of the light-sensitive tissue is compensated for the reduced amount of light within the preselected frequency range to approximate an image of the light-sensitive tissue under the multispectral illumination.

A method of displaying an image of light-sensitive tissue according to an embodiment of the current invention includes illuminating the light-sensitive tissue with multispectral light for a first period of time, imaging the light-sensitive tissue over the first period of time upon being illuminated with the multispectral light, and displaying the image of the light-sensitive tissue for a second period of time that is longer than the first period of time. The second period of time includes a period of time in which the light-sensitive tissue is free of the multispectral illumination, and the imaging the light-sensitive tissue includes compensating for the period of time in which the light-sensitive tissue is free of the multispectral illumination to approximate an image of the light-sensitive tissue as it would appear had it been under the multispectral illumination for the entire second period of time.

BRIEF DESCRIPTION OF THE DRAWINGS

Further objectives and advantages will become apparent from a consideration of the description, drawings, and examples.

FIG. 11A provides a plot of estimated phototoxicity levels and recoloring error for both ASR and AASR according to embodiments of the current invention. Notice that AASR is less phototoxic than ASR for every recoloring error level.

FIG. 11B shows an example image sequence of a membrane peel according to an embodiment of the current invention: Ground Truth (top), white and non-white illumination images triggered by AASR (middle) and AASR image recolorization (bottom).

DETAILED DESCRIPTION

Figure 1:
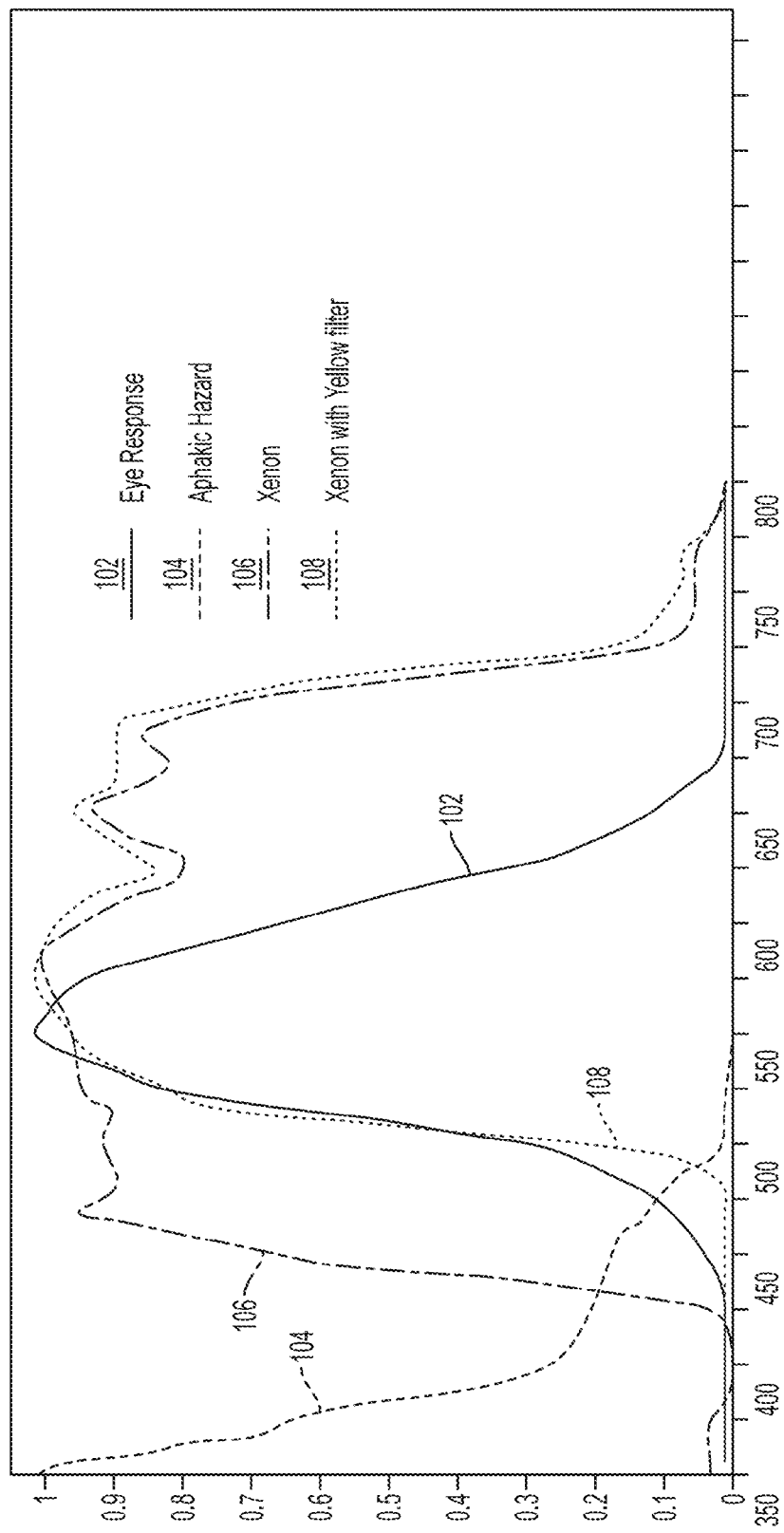
FIG. 1 is a graph of human eye response, aphakic hazard, xenon and xenon with yellow filter spectra.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of the current invention include an illumination system that reduces the risks of phototoxicity for patients undergoing photosensitive surgery. Typical white light illumination used during such surgery may induce trauma in photosensitive tissues within the body. The most striking example of this is vitreoretinal surgery performed on the retina. Being highly sensitive to light, the retina is easily damaged by white light. This is of critical concern for surgeons and patients, because a perfectly performed surgery may yet achieve poor results in terms of patient vision due to phototoxic trauma incurred during the procedure. Thus, a system that reduces the occurrence and risk of phototoxicity during retinal surgery could have very significant and far-reaching impact.

Another aspect of some embodiments of the current invention includes a multispectral programmable light source that has the capability of integrating different spectral emissions in various ways to support special purpose tasks. As an example, a surgeon may use a fluorescent dye as an aid to visualize an anatomical feature for performance of a surgical task. Such a dye could be activated by exposure to specific wavelengths of light. A light source that activates fluorescence on-demand by selectively emitting these wavelengths would support such a procedure. An additional example includes selective use of IR light to provide a slightly different view of the retinal surface. Although IR is not visible to the human eye, it is visible to the cameras used by the illumination system according to some embodiments of the current invention. Because IR penetrates more deeply into tissue than visible wavelengths, its use may improve observation of anatomy lying just below the retinal surface. Furthermore, IR light has very low phototoxicity and may therefore double as an ultra-safe method of illuminating photo-sensitive tissues.

We present a novel observation system according to some embodiments of the current invention that can be used to significantly reduce the emission of highly toxic wavelengths over existing systems. While changing the spectral composition of the illumination toward longer wavelengths could help reduce phototoxicity, we have created a new device according to some embodiments of the current invention which cyclicly illuminates the retina using white light and less damaging non-white light, allowing for maximal phototoxicity reduction. Consequently, images provided by this device are fully colored, monochromatic, or have varying intensities of different portions of the normally visible "white light" spectrum.

To avoid visually straining a potential user (e.g., a surgeon) this device can include an image recoloring scheme. Computer colorization schemes have existed since the 70's (Museum of Broadcast Communication: Encyclopedia of Television (online), http://www.museum.tv/archives/etv/c/htmlc/colorization/colorization.htm) and have since been further developed (Skora, D., Burinek, J., Zra, J.: Unsupervised colorization of black and white car-toons. In: Int. Symp. NPAR, Annecy, pp. 121-127 (2004); Yatziv, L., Sapiro, G.: Fast image and video colorization using chrominance blending. IEEE Transactions on Image Processing 15, 1120-1129 (2006)). In general, however, such systems rely on a user to pre-select regions of the image that correspond to specific colors, making them ill-suited for this application. More recently, a time series analysis was proposed to model the retinal image scene (Sznitman, R., Lin, H., Manaswi, G., Hager, G.: Active background modeling: Ac-tors on a stage. In: International Conference on Computer Vision, Workshop on Visual Surveillance (2009)). This method however relies on having all visual cues (e.g. color and texture) available at all times to maintain an accurate retina model. To our knowledge, no previous work has focused on fusing images taken under varying spectrum illumination to form continuous and coherent image sequences.

Our approach to a low phototoxicity light source capitalizes on unique capabilities afforded through the use of video microscopy. Using video microscopy to indirectly observe retinal surgery, rather than viewing the procedure directly through an optical microscope, allows white light exposure to be reduced in at least the following ways, each of which will be described in more detail:

1. Camera Shutter Synchronization: Enables illumination only when the camera shutter is open; disables illumination when the camera shutter closes following capture of each video frame.

2. Multiplexed Spectrum Imaging: This technique involves changing the light emission spectrum between successive video frames. Frames illuminated by white light are interleaved between frames illuminated by reduced phototoxicity light (e.g., red light) at a repeating interval. Tool tracking and background registration techniques are then used to map color information from the most recent white frame (which appears in full-color) to all subsequently captured red frames (which appear in mono-color). By this method, the video feed is converted to full-color for all frames.

3. Color Companding of Phototoxic Wavelengths: This method performs color companding of highly phototoxic light by reducing the intensity of the most harmful wavelengths in the emission spectrum and subsequently applying a color boost model to the captured video image that computationally boosts the color information corresponding to the attenuated wavelengths. In this way, a full-color image with normal color-balance can be rendered from an illumination spectrum having heavy bias towards low phototoxic regions of the visible spectrum.

4. Adaptive Multispectral Imaging: This technique involves interleaving frames of light with different spectra (as in multiplexed spectrum imaging) or varying the intensity of phototoxic wavelengths (as in color companding) or both in combination, in which a computer automatically varies the fraction of white light to other frames or the relative fraction of phototoxic light based on processing of video images captured during the procedure. For example, the computer might temporarily increase the ratio of white light images to red light frames if the scene is rapidly changing or a tool is moving rapidly across the background.

Any combination of each of these four techniques could also be used in other embodiments of the current invention. Furthermore, the general concepts of the current invention are not limited to only these particular embodiments.

Figure 2:
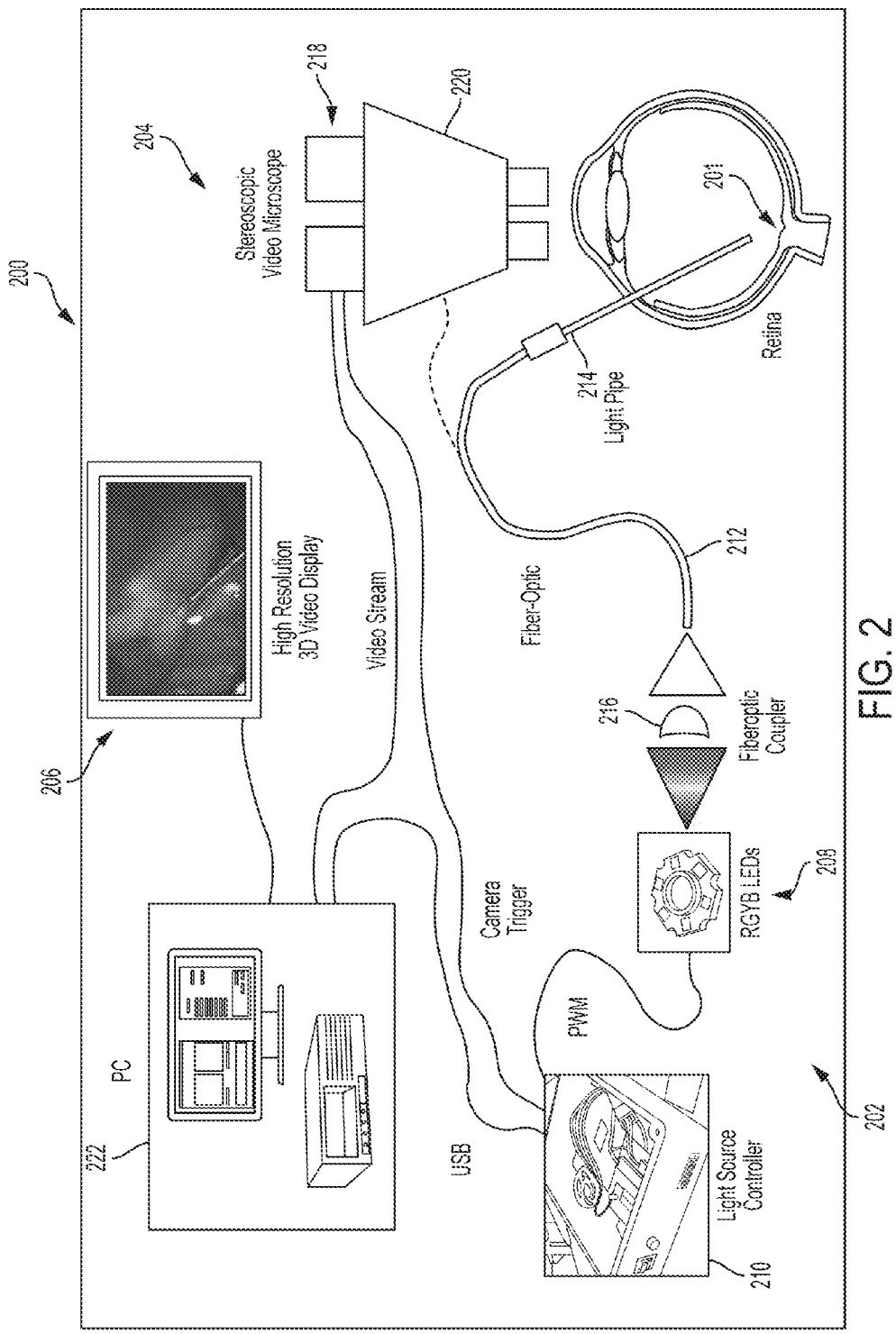
FIG. 2 is a schematic illustration of an observation system for viewing light-sensitive tissue according to an embodiment of the current invention.

FIG. 2 is a schematic illustration of an observation system 200 for viewing light-sensitive tissue 201 according to an embodiment of the current invention. The observation system 200 includes an illumination system 202 configured to illuminate the light-sensitive tissue 201, an imaging system 204 configured to image at least a portion of the light-sensitive tissue 201 upon being illuminated by the illumination system 202, and an image display system 206 in communication with the imaging system 204 to display an image of the portion of the light-sensitive tissue 201. The illumination system 202 is configured to illuminate the light-sensitive tissue 201 with a reduced amount of light within a preselected frequency range compared to multispectral illumination light. For example, the illumination system can be constructed to provide illumination light that uses less of a certain wavelength range of light, such as, but not limited to, toxic light, relative to light that normally would be provided to obtain a certain image quality. This "less amount" can be relative to multispectral illumination that would ordinarily be performed, such as, but not limited to, substantially white light illumination. Furthermore, such a relative reduction can be achieved by spectral, spatial and/or temporal illumination processes, for example. The image of the portion of the light-sensitive tissue is compensated for the reduced amount of light within the preselected frequency range to better approximate an image of the light-sensitive tissue 201 under said multispectral illumination. For example, some embodiments can include, but are not limited to, illuminating with light that is reduced in an amount of toxic light relative to illumination with substantially white light illumination and then compensating the image to appear more like a white-light illuminated image. The term "compensating" is intended to have a broad meaning with respect to various embodiments. For example, the compensation can include, but is not limited to, making an intermittent image appear continuous and/or other processing to counter effects of the reduced relative amount of illumination in the preselected wavelength range. The term "white light" is intended to have a broad meaning to include multispectral light in the visible spectrum with spectral characteristics similar to those normally encountered in circumstances that permit normal color vision. It is not intended to mean an exact, particular spectral composition. Furthermore, the term "substantially white light" can include cases in which the light would actually appear off white with perhaps some slight color.

In the embodiment of FIG. 2, the illumination system 202 includes a light source 208 and a light source controller 210 constructed and arranged to control at least one of a spectral composition and intensity of light that illuminates the light-sensitive tissue 201. In the embodiment of FIG. 2, the light source controller 210 is an electronic control module that is in communication with the light source 208 and the imaging system 204. However, other embodiments could include other ways to control the light output of the illumination system 202 such as other types of light sources, mechanical choppers to chop an illumination beam and/or other types of optical components such as optical filter, prisms and/or lenses. In some embodiments, the illumination system 202 can include and/or be coupled to other optical components to enable illumination of the light-sensitive tissue 201. For example, the illumination system can include an optical fiber 212 attached to a light pipe 214 according to some embodiments of the current invention. The illumination system 202 can include a fiber-optic coupler 216 to couple light emitted from the light source 208 into the optical fiber 212.

The imaging system 204 includes one or more imaging optical detectors 218. In some embodiments, the imaging system may be adapted to attach to and/or include a stereoscopic video microscope 220, for example, as is illustrated schematically in FIG. 2. The imaging system 204 can be arranged to image the light-sensitive tissue 201 and can be in communication with the light source controller 210 of the illumination system 202. In some embodiments, the imaging system can include other electronic components to process image data from the imaging optical detectors. For example, the imaging system can include a PC or other computer 222 and/or other data processing and/or storage system to process imaging data from the imaging optical detectors 218. The PC or computer 222 can also be in communication with the illumination system 202, such as with the light source controller 210 according to some embodiments of the current invention. The data communications channels between the various components shown in FIG. 2 can be hard-wired electrical connections, optical connections and/or wireless connections, for example, or may use other data communications devices or techniques.

In one embodiment, the light source controller 210 causes the light-sensitive tissue 201 to be illuminated by substantially white light for a first period of time and to be free of illumination from the illumination system for a second period of time thus providing the reduced amount of light within said preselected frequency range. For example, the light source controller 210 turns LEDs in the light source 208 on and off. The light source controller 210 further communicates with the imaging system 204 such that image acquisition is performed during the first period of time while the light-sensitive tissue 201 is being illuminated with substantially white light and image acquisition is stopped for the second period of time. The white light illumination can be performed by turning on red, green and blue LEDs in the light source 208, for example. In the example of FIG. 2, red, green, yellow and blue LEDs are used to obtain a better quality white-light spectrum. The image display system 206 displays an image of the portion of the light-sensitive tissue 201 based on the image acquisition over the first period of time to extend over both the first and second periods of time to appear more like an uninterrupted white-light-illuminated image. In other words, the image acquisition can be synchronized with the periods of illumination according to one embodiment of the current invention such that it appears that the light-sensitive tissue 201 is being continuously illuminated; however, in actuality, there is no illumination over portions of the observation period. In some embodiments, the light source 208 can also include one or more LEDs to emit infrared light. This can be useful for imaging the infrared light and/or for observing fluorescent light from a fluorescent dye introduced for particular imaging purposes, for example.

The imaging optical detectors 218 of the imaging system 204 can include a plurality of optical detection elements that each having a spectral sensitivity that substantially matches a spectral emission of a corresponding one of said plurality of light-emitting diodes. For example, the imaging optical detectors 218 may include detection elements that are each optimized to detect one of red, green, yellow and blue light corresponding to the emission spectrum of the light source 208. In addition, in cases in which the light source includes an infrared emitter, the detection elements of the imaging optical detectors 218 can be optimized to detect infrared light of the frequencies emitted by the infrared emitter. When the sensitivity of the detection element is relatively good at a frequency of relatively strong emission of an emitter, we can say the detection element and the emitter are substantially matched.

In another embodiment, the light source controller 210 causes the light-sensitive tissue 201 to be illuminated by substantially white light for a first period of time and to be illuminated by substantially red light for a second period of time thus providing the reduced amount of light within the preselected frequency range. (One should note however that this does not have to be only red light. It could be any illumination spectrum having lower phototoxicity than white light. Red is chosen as one embodiment because it is the least phototoxic of all visible wavelengths. However, IR and other combinations of visible light could be used as well.) For example, the RGYB LEDs in the embodiment of FIG. 2 could all be turned on for a period of time followed by a period in which the red LED is turned on. The light source controller 210 communicates with the imaging system 204 such that imaging data acquired during the first period of time while being illuminated with substantially white light is used to compensate imaging data acquired over the second period of time such that the image displayed by the image display system appears more like an uninterrupted white-light-illuminated image. Clearly, other embodiments of the current invention could include various combinations of periods of white light, red light and no illumination. In this embodiment, the imaging system 204 can further perform the compensation such that at least one of background image portions or images of tools within the image are segmented from the light-sensitive tissue. Such background portions of the image and/or objects within the field of view such as tools that are being used during surgery, for example, can make it more difficult for an observer when view in monochromatic imaging, Therefore, segmentation and colorization can be performed, for example using PC or computer 222, according to some embodiments of the current invention.

In other embodiments, The light source controller 210 causes the light-sensitive tissue to be illuminated by light having a reduced amount of light at wavelengths that are harmful to the light-sensitive tissue 201 relative to a white light spectrum, and the imaging system 204 (e.g., using PC or computer 222) is adapted to apply a color boost model to compensate for the reduced amount of light at wavelengths that are harmful to the light-sensitive tissue 201. For example, the blue LED of light source 208 could be turned on for a shorter period of time than those of the other colors, or made less bright than it typically would be for a well-adjusted white light source, to reduce the amount of light at wavelengths that are harmful to the light-sensitive tissue 201. In some embodiments, filters could be used instead of, or in addition to, the above-noted mechanism, for example. The color boost model can be or include companding, for example.

EXAMPLES

In order to implement examples of phototoxicity reduction techniques according to some embodiments of the current invention, the illumination system is provided with a tunable color spectrum and rapid turn-on/turn-off light emission. To satisfy these requirements, an LED-based solution has been chosen with red, green, blue, and yellow LED channels. However, the general concepts of the invention are not limited to this particular example. Other types of light sources could be used as well as other combinations of LED spectral properties. Furthermore, infrared LEDs could also be included for imaging and/or used with fluorophores, for example. According to this embodiment, independent control of each color channel provides highly tunable color temperature and excellent color rendering index (CRI).

Example System Overview

The heart of the illumination system according to this example is the Light Source Controller (LSC), which controls low-level modulation of the LEDs and synchronizes illumination activity with video camera shuttering. The computational power of the LSC is provided by a PIC24F microcontroller; further detail concerning the LSC electronics design is provided in provisional application Ser. No. 61/325,647 to which the current application claim priority and the entire contents of which are hereby incorporated by reference. The LSC's illumination and synchronization settings are controlled from a PC, which communicates with the LSC via either USB or serial port (RS-232). A user controls the illumination system using a graphical user interface (GUI) application running on a PC. Alternatively, the illumination system may be controlled by any other autonomous, semi-autonomous, or user-driven PC application that sends appropriate commands to the LSC. Appendix A in provisional application Ser. No. 61/325,647, the entire contents of which are hereby incorporated by reference, also describes the particular software architecture for the system, including firmware for the LSC's embedded electronics and the PC application for user level control.

The LSC is an embedded, stand-alone device that modulates four LED control channels and synchronizes camera shuttering. Illumination of each LED channel is controlled via pulse width modulation (PWM) using a PWM period of 100 microseconds. Adjustment of the PWM duty cycles provides independent brightness control over each LED channel. The LSC synchronizes illumination and camera shuttering using a triggering signal sent at the start of capture for each video frame. This trigger may function either as an output, where the LSC is the trigger source and initiates frame capture, or as an input, where the camera is the source of the trigger, which it sends at the beginning of each video frame. When the trigger functions as output, the LSC sends the trigger at the start of a new frame and activates the LEDs. The LSC then waits for the shutter period of the camera to expire, at which point it deactivates the LEDs. The LEDs remain off until the frame period has expired; this process then repeats for the next frame. During this process, the camera will not begin capture of a frame until it receives the trigger signal from the LSC. Thus, the LSC has complete control over the video frame rate. Similarly, when the trigger functions as input, the camera controls its own frame rate, sending the trigger signal to the LSC at the start of each frame. When the LSC receives this trigger, it illuminates the LEDs until the shutter time of the camera has expired. At this point, the LSC deactivates the LEDs and waits for the next trigger signal from the camera. By controlling/monitoring when each video frame begins, the LSC ensures perfect synchronization between illumination activity and camera shuttering.

Although the illustrated LSC supports four LED channels, the illumination system easily may be extended to include any number of LED channels. This is done by using multiple LSCs and daisy-chaining the camera trigger. Daisy-chaining the trigger is necessary in order to synchronize all LSCs and the camera to the same trigger source. In this topology, all but one of the LSCs (call this the master LSC) will set their trigger as input. The master LSC may then either set its trigger as output, in which case it becomes the trigger source for the camera and all remaining LSCs, or it may set its trigger as input, in which case the camera must source the trigger to all LSCs. To support this daisy-chain feature, an LSC is equipped with two identical trigger connectors that are internally wired together. Thus, all that is required is to connect the camera to one of these connectors on the master LSC and daisy-chain an additional LSC using the other connector. This chain can be extended from the added LSC to yet another LSC and so-on without limit.

Any LED of suitable current rating (refer to Appendix B of 61/325,647 for specs) may be used with the LSC. In practice, any LEDs of any current rating may actually be used by adjusting the current rating of the LED driver electronics used in the light source controller. The LEDs plug into a connector at the back of the LSC; thus, one LED configuration may be readily swapped for another. The LEDs chosen for this example are ACULED VHL LEDs from Perkin Elmer Optoelectronics in the RGYB configuration (having an LED of color red, green, yellow, and blue). This product uses chip-on-board technology to package four very high lumen LEDs onto a single chip. Having all four LEDs on one chip provides an advantage of excellent color mixing due to the close proximity of one LED to another.

Light from the LEDs may be delivered to the target via a variety of methods. The simplest method is to shine the LEDs directly onto the target. For this method, mounting a short fiber bundle rod directly above the LED chip helps focus the light and achieve optimal color mixing. Shining the LED directly over the target is not always the most convenient method, however, and may not even be feasible for applications such as retinal surgery. Another method for retinal surgery applications is to mount the LEDs at the optical input to the surgical microscope. Another method for retinal surgery, frequently preferred by surgeons, may be to couple the light into a fiber-optic light pipe, which is then inserted through the sclera of the eye. Much light is typically lost in the process of coupling light into a small fiber. This is complicated by the very wide angle of divergence of light emitted from the ACULED LEDs. Thus, intense light brightness is required. A typical light intensity for commercial fiber-optic light sources for retinal surgery is 10 lumens of light output from the fiber at maximum intensity (Chow, David, MD. "Shedding Some Light on Current Endoillumination: Brighter Light can be Safe Light". Retinal Physician. January 2005. Retrieved from http://www.retinalphysician.com/article.aspx?article=100050). The maximum output of an ACULED VHL RGYB LED is 189 lumens (Perkin Elmer Optoelectronics. *ACULED® VHL™ Standard White, Monochromatic and Multi-Colored Four-Chip LED Products*. 2008). Numerous approaches to accomplish capturing enough light into a fiber have been used and others are anticipated. The specific method chosen to couple light into the fiber is not an element of this invention, and any method known in the art may be used, so long as sufficient light is provided to the imaging system for the purpose of acquiring images. For some applications, it has not been necessary to have brightness equivalent to commercial systems while using a light pipe; thus, somewhat lower brightness levels may been tolerated. Using other methods for light delivery, such as the microscope's optical input, provides much higher brightness because of the wide diameter of the optical channel. This method has proven quite adequate for some applications.

Two video cameras mounted on a surgical microscope provide a high-resolution video feed in 3D. Any camera supporting suitable triggering capability could be used. For this setup, the Flea2 FL2-08S2C FireWire cameras from Point Grey Research are used, which provide a resolution of 1024× 768 at 30 Hz. The video is displayed to the user in 3D using a 3D-capable LCD screen; viewing the scene in 3D requires the user to wear special polarizing glasses made for this purpose.

The techniques employed in these examples to accomplish phototoxicity reduction while using this illumination system are now discussed.

Phototoxicity Reduction Technique #1: Camera Shutter Synchronization

The simplest method employed by the illumination system to reduce phototoxicity is to switch off the LEDs throughout the period when the video camera's shutter is closed. The shutter of a video camera is typically open for only a fraction of each video frame period. The shutter time is typically controllable by the user and can be set to any desired value. The shutter period must be long enough to capture enough photons to produce a clear, bright image, but not so long that pixels in the image saturate or image blurring occurs due to motion in the scene. Even for extended shutter times, the shutter will typically close prior to the end of the frame period in order to allow time for data transfer of the captured image (certain triggering modes on some cameras allow image capture and data transfer to occur simultaneously).

As an example case, consider a video stream running at 30 Hz; the time interval between each frame is 33 milliseconds. If the shutter period is around 15-20 milliseconds (a typical setting for good image quality in our experience) then the shutter is closed for about 50% of the frame period. Disabling illumination during this period reduces light output by the same fraction. For slower frame rates, the fractional reduction in light output is even more dramatic. Provided that the relationship between phototoxicity and total light exposure is approximately linear, this scenario would reduce phototoxicity by about 50%. We are currently conducting phototoxicity trials to determine what the relationship between light output and phototoxicity really is in practice.

Figure 3:
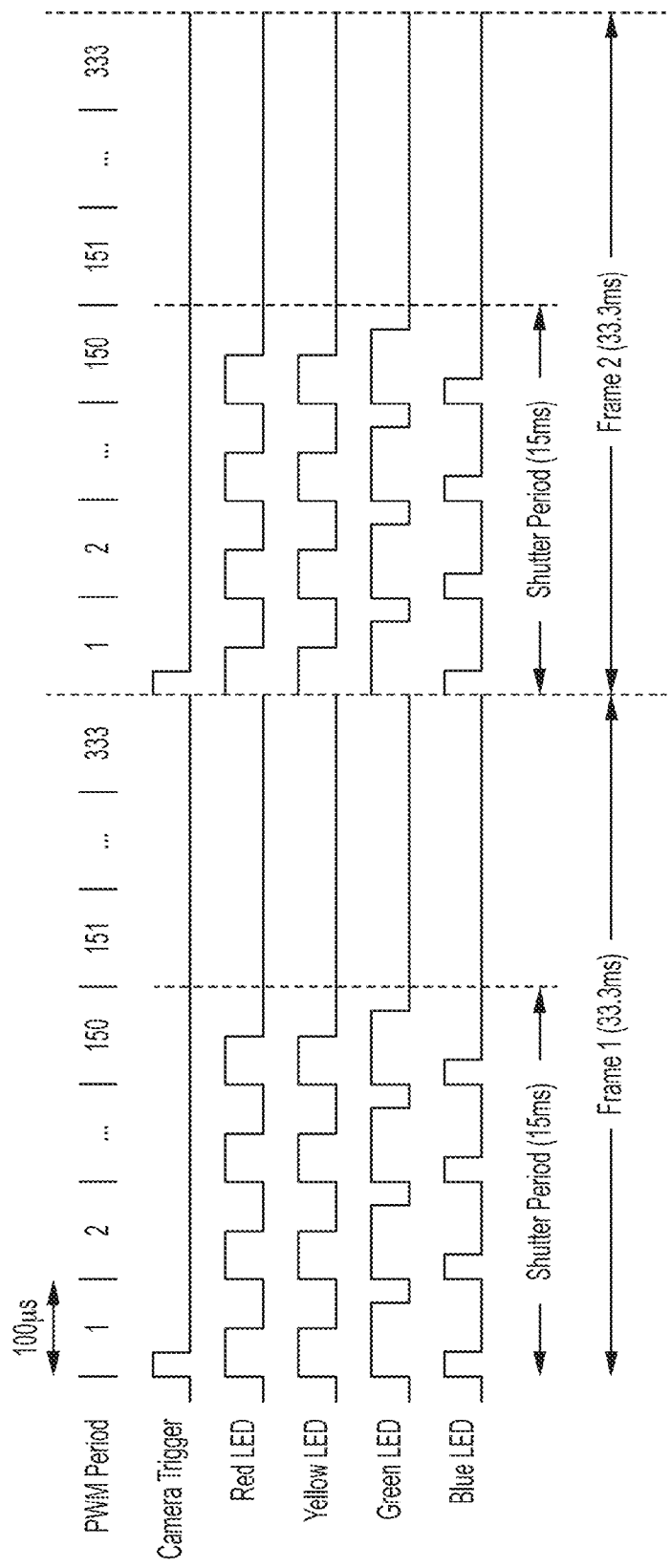
FIG. 3 shows the LED and camera trigger waveforms used in one example according to an embodiment of the current invention.

To aid understanding of the illumination system's operation, FIG. 3 shows the LED and camera trigger waveforms corresponding to this phototoxicity reduction technique. The figure assumes a frame rate of 30 Hz. As seen in the figure, LED brightness is controlled using a PWM period of 100 microseconds. Thus, 333 PWM periods comprise one complete frame time of 33.3 milliseconds. The LEDs are only active during the open shutter period of the camera, which in this example occurs during the first 15 milliseconds of each frame. The LEDs are shown operating at different duty cycles: red at 50%, yellow at 50%, green at 75%, and blue at 25%. As a point of note, when two LEDs have the same duty cycle it does not necessarily mean they output the same brightness. In this case, they output the same fraction of their maximum brightness, but the maximum brightness is typically much different for LEDs of different color because of the differences in material properties used to create LEDs of different color. The luminal output of the LEDs used for this research is published in the ACULED VHL datasheet. Also notice in the figure that the camera trigger signals the start of each frame period.

Phototoxicity Reduction Technique #2: Multiplexed Spectrum Imaging

Figure 4:
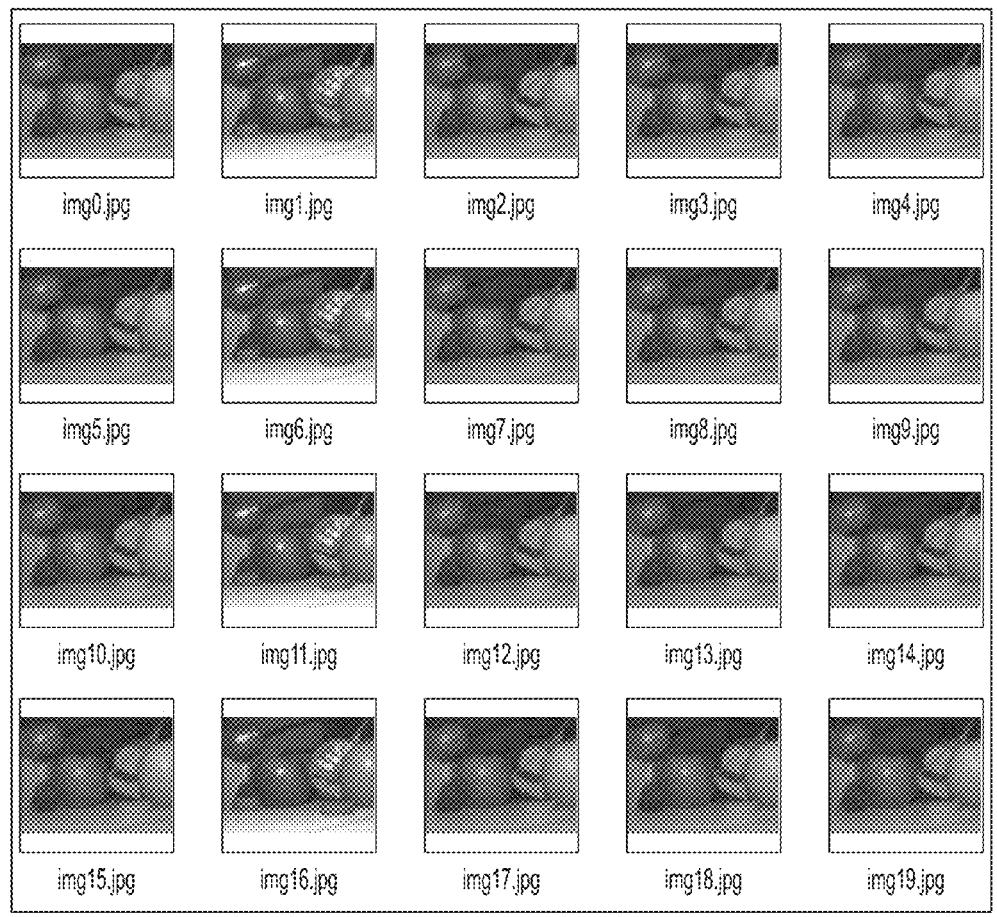
FIG. 4 shows images demonstrating an example of video sequences showing one frame illuminated by white light for every four red light frames according to an embodiment of the current invention.

The second technique used to reduce phototoxicity is to use varying light spectrums to illuminate consecutive video frames in repeating sequence. Because the LSC knows when each frame capture begins, it can choose different light spectrums to illuminate different frames. The way this method reduces phototoxicity is by interleaving frames illuminated by a white light spectrum in between frames illuminated by a red light spectrum. White light contains all visible wavelengths and is therefore highly phototoxic; red light, on the other hand, has very low phototoxicity. Alternatively, IR light could also be used in place of red light for even lower phototoxicity. FIG. 4 demonstrates an example video sequence showing one frame illuminated by white light for every four red light frames.

As seen in FIG. 4, images captured under a light spectrum other than white light contain incomplete color information. Some method is therefore required to restore color to images captured under the low phototoxicity spectrum. Without this, the video feed would flicker between full-color and red-color images in a very distracting manner. Color flicker is eliminated from the video feed by mapping color information from the most recent white light image to all subsequent images captured under a low phototoxicity spectrum (i.e. red light). White image frames are displayed with no alteration, since they contain complete color information. When displaying red images, the algorithm works by registering the image background of the red image with the background of the last acquired white light image. Foreground objects are also segmented from the images and tracked. Color information is then mapped from the background of the white light image to corresponding pixels in the background of the red image. This renders the image background in full-color. Foreground objects in the red image, such as surgical tools, are colored using a tool model, since the corresponding pixels for these objects are harder to identify and may not even be present in the white light image. The end result is a video feed rendered in continuous full-color from a raw video stream having alternating full-color and red-color images. The registration, tracking, and color mapping algorithms employed for this technique are further described in detail in a paper presented at the 2010 IPCAI conference (Sznitman, R., Billings, S., Diego, R., Mirota, D., Yang, Y., Handa, J., Gehlbach, P., Kang, J., Hager, G., Taylor, R., *Active Multispectral Illumination and Image Fusion for Retinal Microsurgery*. The Johns Hopkins University. Information Processing in Computer Assisted Interventions (IPCAI) Conference, Geneva, June 2010, the entire contents of which are incorporated herein by reference). Using this phototoxicity reduction technique, the damaging impact of highly phototoxic wavelengths is reduced while still preserving the color information that these wavelengths provide.

The LSC provides a command for specifying an interval at which a white light spectrum is to be intermixed with a low phototoxicity spectrum. This interval is referred to as the "dark frame interval". The dark frame interval sets the number of sequential frames to be illuminated by the low phototoxicity spectrum following each frame illuminated by white light. Thus, a dark frame interval of zero results in all frames being illuminated by white light. A dark frame interval of one results in every other frame being illuminated by white light, reducing white light exposure by 50%. Larger dark frame intervals provide progressively greater reduction in white light exposure, thereby reducing phototoxicity. The video sequence shown in FIG. 4 has a dark frame interval of four. Typically, the dark frame interval is set by the user via the GUI application. This interval could also be dynamically updated using an algorithmic-based solution. For example, the color mapping algorithm may be programmed to adjust the dark frame interval based on certain metrics of image quality.

Image Recoloring Examples

From the device described above, white and red light images are cyclically produced at a fixed rate. Naturally, emitting fewer white light images allows for lower levels of phototoxicity for the patient. However, reducing the number of white light images increases the difficulty of the procedure for the surgeon. Hence, a method which restricts the number of white light images used, and still provides a typical view for the surgeon, can be provided. Ultimately, it is desired to produce an accurate colored image of the retina at any given time, irrespective of which illumination was used.

To provide a coherent colored image sequence according to the current embodiment, we present two methods: a naive and an active scene rendering approach. Due to the lack of previous work on this particular topic, we treat the naive approach as a baseline algorithm. This algorithm is simple and may be most useful only in cases with high fractions of white light. We also compare both methods on image sequences where ground truth is available, thus demonstrating improvements produced by non-naive methods.

At each discrete time step, t, we denote the type of illumination the device is triggering as $L_t$, where $L_t=1$ when white light is used, and $L_t=0$ for non-white light. Associated with each illumination, $I_t=\{R_t, G_t, B_t\}$ is the corresponding RGB image acquired. The rate at which white light illuminates the retina is then defined as $$\phi = \frac{\sum_{i=1}^{t} L_i}{t} \quad (1)$$

In order to perform recoloring, it is necessary to correctly account for the color of the non-white illuminant. We define the color space of the acquired images as the usual RGB color space denoted by $S \subset R(3)$. Following (Mallick, S., Zickler, T., Belhumeur, P., Kriegman, D.: Specularity removal in images and videos: A PDE approach. European Conference on Computer Vision (2006) 550-563), we define a separate color space $S' \subset R(3)$ such that the color of the non-white illuminant is (1,0,0). We relate S and S' by a linear transformation A of the form A=sR, where s is a scale factor and R is a rotation. Then for any RGB value $p \in S$, we can compute $p' \in S'$ as $p'=Ap$. The optimal A can be computed by first acquiring a non-white illuminated image, finding the largest principal component, x, and subsequently constructing two orthogonal components y and z as in (Mallick et al., ibid). R is constructed from these components. The scale s can then be computed by comparing a while light and non-white light image under the (color) rotation R.

Since our non-white illuminant is largely red, in the remainder of this example we will continue to refer to the non-white image as the "red" image and the two orthogonal components as green and blue with the understanding that these are, in general, not the raw color values from the camera.

We denote $F_t$ as the final fully colored image rendered by our system. As the device sequentially provides us with images, we will maintain a color model for the retina, $M=\{m_G, m_B\}$, where $m_B$ and $m_G$ are the green and blue color models (represented in the form of images), respectively. Such a color model will be maintained over time, and we thus denote $M_t$ as the color model at time t. In order to have a color model at any given time, t, let $I_1$ be a white light image.

Naive Approach

Perhaps the simplest method to create and maintain a colored image model, $M_t$ is to assume that images do not significantly change over time. In other words, a strong continuity in the appearance in color from $I_t$ to $I_{t+\delta t}$ is assumed.

Figure 5A:
FIG. 5A shows an example of a non-white light image from a device according to an embodiment of the current invention and FIG. 5B shows the image rendered by the naive algorithm. Notice that simply using the G and B channels from the last white frame does not generate good color images. This is particularly the case when there is motion in the scene.
Figure 5B:
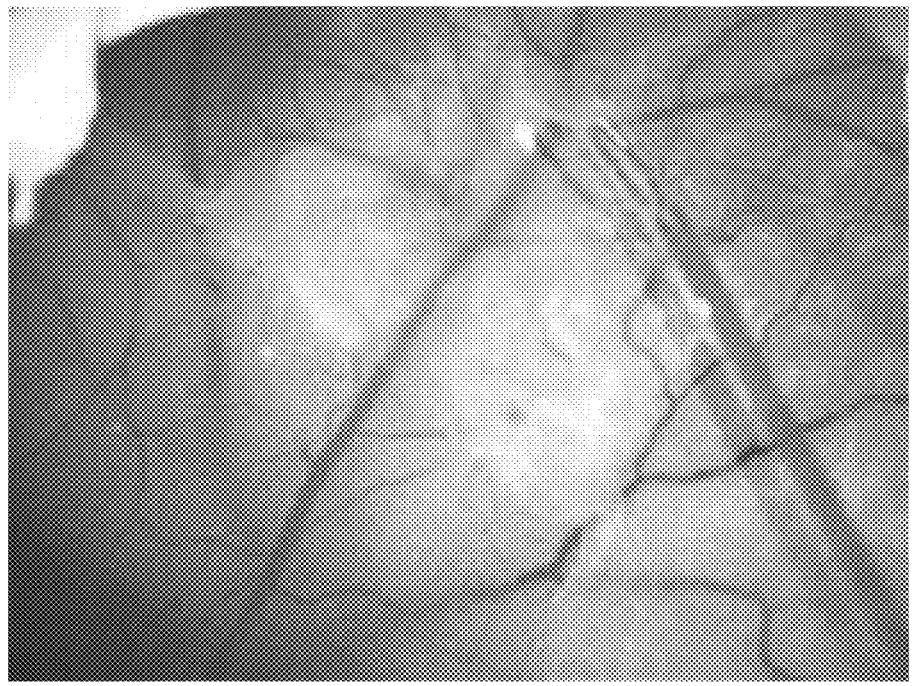

The corresponding algorithm is simple: if $L_t=1$, then the model $M_t$ is updated, $M_t=\{G_t, B_t\}$ and $F_t=I_t$. Otherwise, $L_t=0$ and we let $F_t=(R_t, m_G, m_B)$. Following such a procedures ensures that all $F_t$ are fully colored images. FIGS. 5A and 5B show an example and $I_t$ and $F_t$, respectively. Notice that continuity is violated, as the tool has been displaced since the last white-light image received, thus causing "ghosting" effects.

Active Scene Rendering Approach

A natural extension of the naive approach is to infer the motion observed in the image sequence and correct the associated artifacts. We present our novel color fusing algorithm: Active Scene Rendering (ASR). Here the idea is to estimate the different forms of motion which appear in the scene and take this information into account when rendering the colored images.

Here, it is still assumed that a strong temporal correlation between adjacent images is present. Furthermore, it is stipulated that a transformation, T, from image $I_t$ to $I_{t+1}$ can be inferred. Intuitively, T can be regarded as the motion, induced by the surgeon, which the eye undergoes during a procedure. Notice that this transformation only accounts for the eye motion and not the tool motion. Hence, to further reduce colorization errors (as those in FIG. 5B), we model the tool and its motion as well. The idea is to first detect the pose of the tool to obtain a 2D segmentation and then use this information to recolor the image correctly. We now describe how the estimation of the transformation T and the 2D tool segmentation are performed.

Image Stabilization. As previously mentioned, the surgeon is free to manipulate the eye. To compensate for this motion, a simple translation model for the motion of the retina is assumed. Although it has been shown that wide angle retinal image deformation is best modeled with a quadratic deformation (Stewart, C., Chia-Ling, T., Roysam, B.: The dual-bootstrap iterative closest point algorithm with application to retinal image registration. Medical Imaging, IEEE Transactions on 22(11) (November 2003) 1379-1394), small motion can be approximated with pure translation when under high magnification. To estimate the translation we first extract SIFT features (Lowe, D.: Distinctive image features from scale-invariant keypoints. International Journal of Computer Vision 20 (2003) 91-110) ($I_t$ is treated as a gray scale image for any value of $L_t$), find correspondences and then apply the robust ASKC method (Wang, H., Mirota, D., Hager, G.: A generalized kernel consensus based robust estimator. IEEE Transactions on Pattern Analysis and Machine Intelligence 32(1) (2010) 178-184) to find the translation that best explains the correspondences. This permits us to find a transformation regardless of whether the tool is present in the image or not. Note that in order to present coherent image sequences, images are cropped by removing border regions.

Tool Detection. Given that the most consistent clue for the tool is its constant and known 3D shape, we use the framework proposed in (Rother, D., Sapiro, G.: Seeing 3D objects in a single 2D image. International Conference on Computer Vision (2009)) for simultaneous segmentation and pose estimation which exploits this information. This framework requires, as input, the 3D shape (represented as voxel occupancies) and color probability distribution (represented as a mixture of Gaussians) of the tool, and the color probability distribution for each background pixel (represented as a single Gaussian). The output of the framework is a segmentation of the tool in each frame, and also an estimate of the 3D pose of the tool in the 3D coordinate system of the camera, for each frame. The estimated 3D pose in one frame is used to initialize the segmentation and pose estimation in the following frame. Using this method guarantees finding the globally optimal 3D pose and segmentation in a computationally efficient manner.

The algorithm for ASR is similar to that of naïve approach described above. At t=1, we let $F_1=I_1$ and set $M_1=\{G_1, B_1\}$. $I_1$ is then treated as the initial frame of reference, such that subsequent images are stabilized with regards to $I_1$. That is, for every new image $I_t$, we compute the transformation $T_t$ from $I_t$ to $I_t$. Then, using $T_t$, we translate $I_t$ and compute a rectified image, $\tilde{I}_t$. When $L_t=1$, we set $M_t=\{\tilde{B}_t, \tilde{G}_t\}$ and $F_t=\tilde{I}_t$.

Figure 6A:
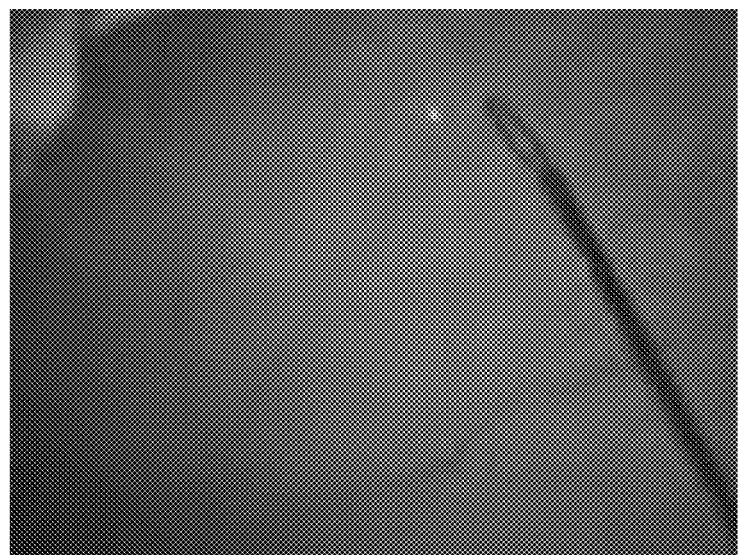
FIG. 6A is an example of a non-white light image from a device according to an embodiment of the current invention.
Figure 6B:
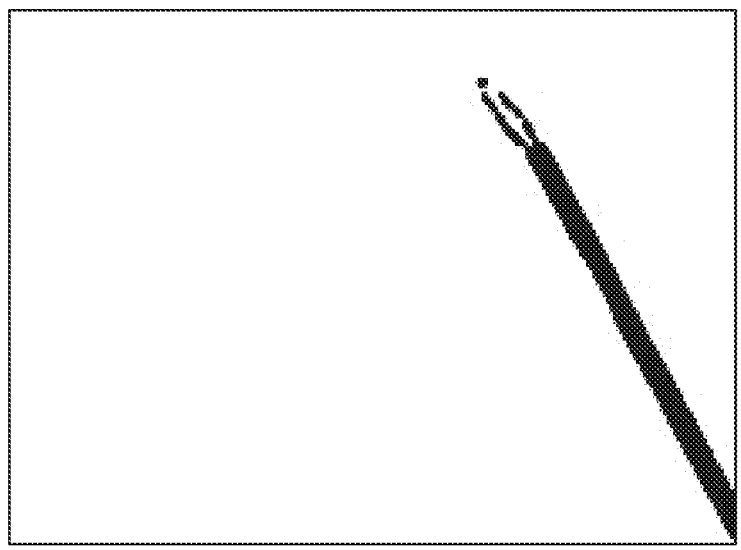
FIG. 6B shows a segmented tool corresponding to FIG. 6A.
Figure 6C:
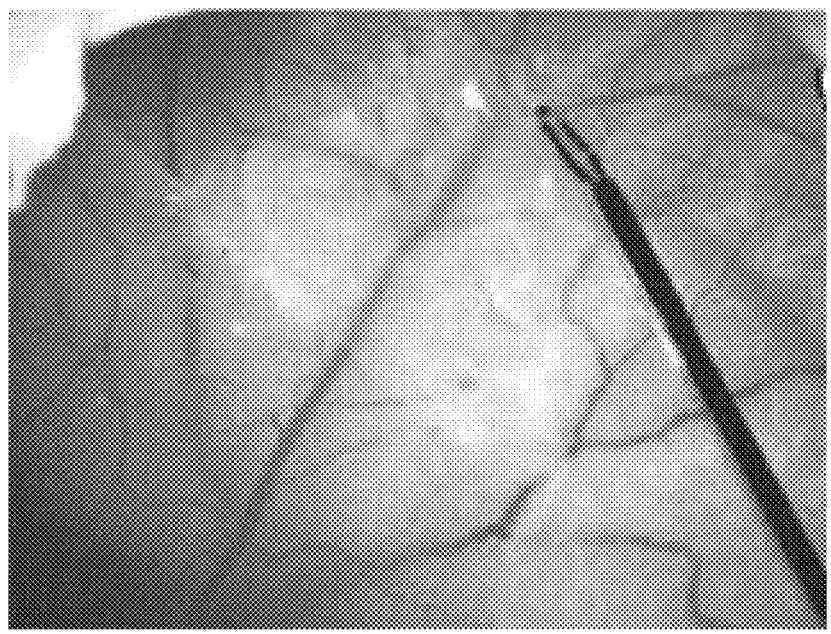
FIG. 6C shows a rendered image by ASR according to an embodiment of the current invention. Here, the tool is correctly estimated and image regions are updated in a coherent manner.

If $L_t=0$ (FIG. 6A), the 2D segmentation of the tool is determined (FIG. 6B). To do this, $M_t$ and the known color model of the tool is used to initialize the detection process described above. Once the segmentation has been computed, this region is rendered using the tool color model. The rest of the image is rendered as $F_t=(\tilde{R}_t, m_G, m_B)$ (FIG. 6C).

Experimentation

We now show how our system performs on phantom image sequences. A quantitative comparison of both methods is described below, where it is shown that ASR surpasses the naive approach in a setting where ground truth is known. This is shown by measuring the error for different values of ϕ. Qualitative results of our system on image sequences are then provided in the section that follows.

Validation with Ground Truth

To validate both approaches described above, we recorded two image sequences of membrane peeling on embryonic eggs using only white light. Doing so allows us to synthetically generate limited-spectrum images at any rate ϕ, by using only the red band of white light images. Hence, we know that the transformation A (see above) is known to be A=I. As detailed in (Leng, T., Miller, J., Bilbao, K., Palanker, D., Huie, P., Blumenkranz, M.: The chick chorioallantoic membrane as a model tissue for surgical retinal research and simulation. Retina 24(3) (2004) 427-434, Fleming, I., Balicki, M., Koo, J., Iordachita, I., Mitchell, B., Handa, J., Hager, G., Taylor, R.: Cooperative robot assistant for retinal microsurgery. International Conference on Medical Image Computing and Computer Assisted Intervention 11(2) (2008) 543-550), this phantom setup provides a similar environment to in-vivo settings. Image sequences consist of 500 images, acquired at 20 frames per second using the system described above. Using this data, 5 image sequences are generated where ϕ={½, ¼, ⅛, 1/16, 1/32}. For each sequence, both naive and ASR colorization approaches are evaluated. Since the ground truth—the original recorded white light images—is always available, an error can be computed for each frame generated by either approach. In the following experiments the L2 (or mean squared error) norm is chosen to measure the error between the ground truth and the rendered images. In addition, we also compute the error using the Bounded Variation (BV) norm, which has been used to quantify image quality during denoising Tasks (Chang, Q., Chem, I.: Acceleration methods for total variation-based image de-noising. SIAM Journal of Applied Mathematics 25(3) (2003) 982-994). This provides us with a measure of image quality, taking into account both photometric and rectification errors.

Figure 7A:
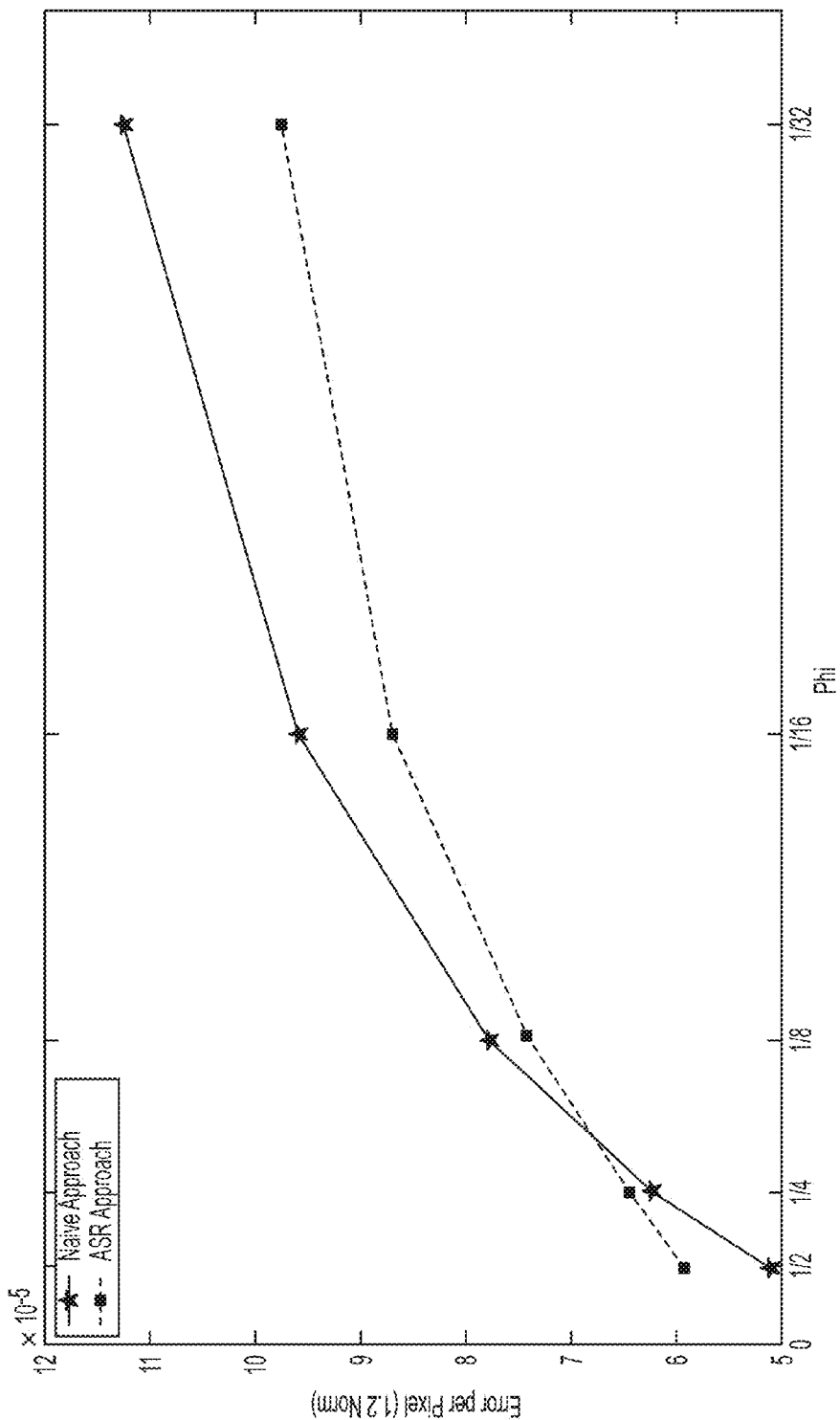
FIGS. 7A and 7B show evaluations of the proposed methods when varying the fraction of available white-light images, $\phi$. The average error per pixel ((FIG. 7A) L2 norm (FIG. 7B) BV norm) is computed on image sequences where ground truth is known. Both error metrics indicate that ASR (dashed line) provides accuracy gains over the naive approach (solid line).
Figure 7B:
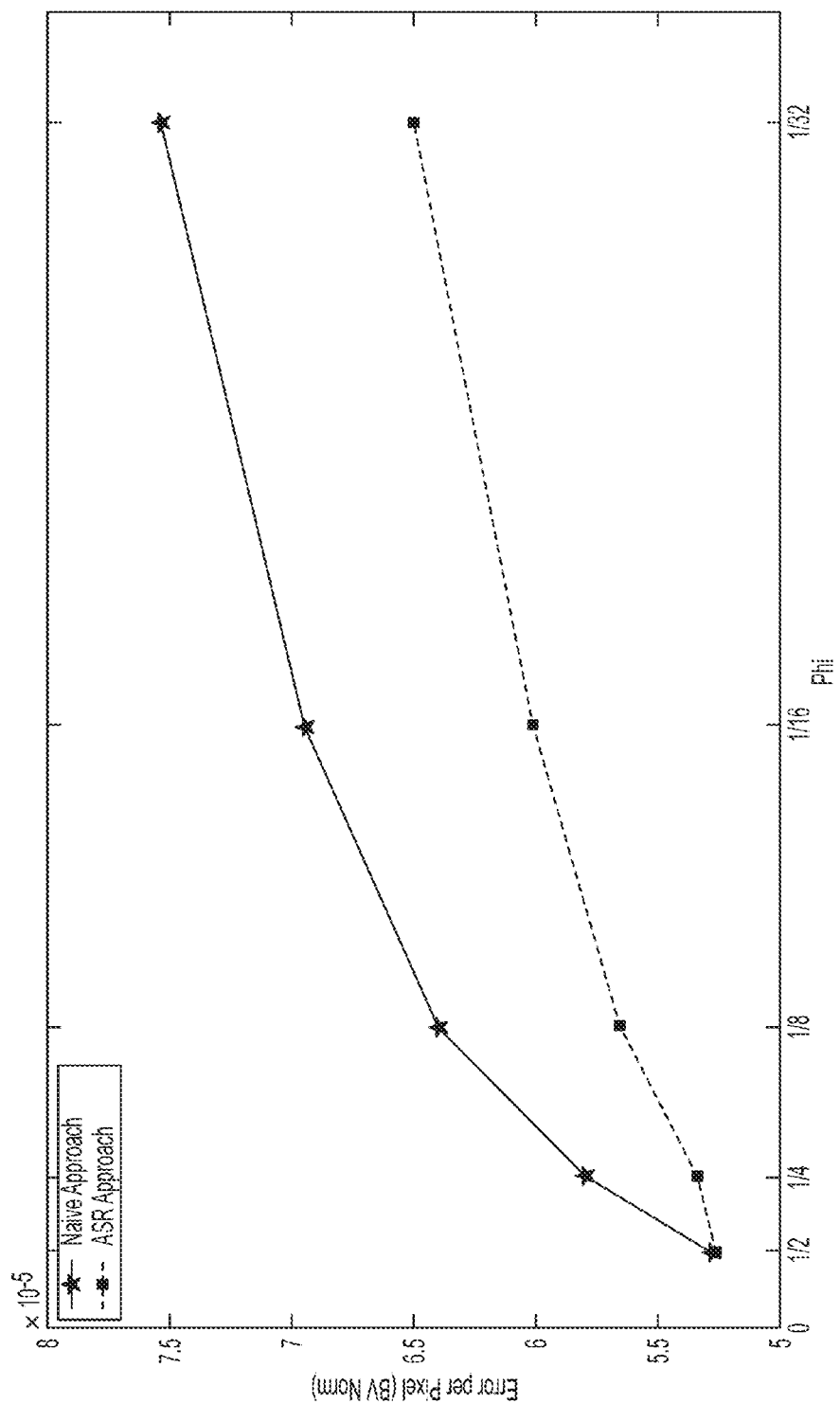

FIG. 7A shows the L2 norm error when varying ϕ for both methods. FIG. 7B shows a similar result for the BV norm. In general, one can observe that as ϕ decreases, the error rate increases. This is expected as the assumption of similarity between frames, discussed above, is increasingly violated. Naturally, the naive approach suffers greatly when ϕ is small, as the true color may differ greatly from the last observed color. ASR however suffers significantly less from small ϕ values, as it is able to maintain a more accurate color model.

Egg Peeling

Now that we have observed that ASR can provide a better way to model retinal-type scenes, we set up our system to record and display images for different values of ϕ. We record several image sequences in a similar setup as above and show the resulting recolored sequence. Note that the color mapping transformation A is assumed to have R=I, and a uniform scaling factor (determined empirically).

Figure 8:
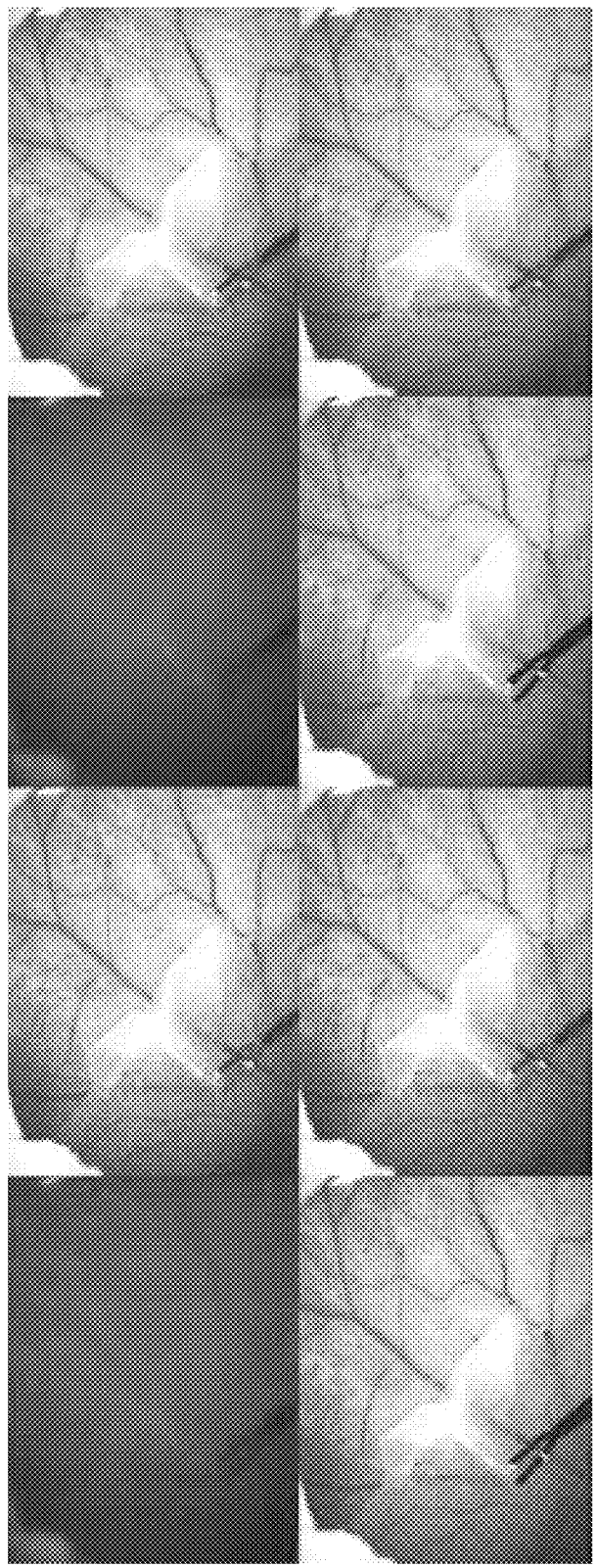
FIG. 8 shows example image sequences from the device ($\phi=\frac{1}{2}$) (top row) and corresponding rendered sequence using ASR (bottom row) according to an embodiment of the current invention.

In FIG. 8 we show a typical image sequence (ϕ=½), of a chorioallatonic membrane peel from an 11 day old chicken embryo. The resulting recolored images rendered by our system are shown. A video recording of this sequence was made. The video shows four similar peeling sequences where each row corresponds to a different ϕ value (½,¼,⅛,1/16). The first column shows the images provided by the device, while the second and third columns show how the naive and model approach, respectively, render the sequence. Since the device is being used to obtain these image sequences, no ground truth is available for quantitative comparison. Notice that in general the model approach renders a more coherent image than the naive approach. This is particularly true at smaller co values, concurring with the results above.

In this example, we have conducted experiments with a novel system according to an embodiment of the current invention that can be used to reduce toxic light exposure in retinal microsurgeries. The system includes a new lighting device which can reduce emission of highly toxic wavelengths. In addition we have developed a novel algorithm that can be used with this device in order to render a fully colored image sequence to the user, thus avoiding visual discomfort. We have shown qualitatively and quantitatively that our method can provide superior rendering over naive approaches. Even at low ϕ rates (e.g. ⅛ or 1/16), we showed that maintaining high color fidelity is possible, allowing for low levels of phototoxicity. However, most retinal surgeries involve changing the structure of the retina, and hence the color of the retina (as described in Sznitman, R., Lin, H., Manaswi, G., Hager, G.: Active background modeling: Actors on a stage. International Conference on Computer Vision, Workshop on Visual Surveillance (2009)). As seen in our image sequences, regions of the retina which are altered by the surgeon cannot be recolored correctly until a new white light image is provided according to this embodiment. Hence a potential improvement of this method would involve a dynamic ϕ, which could change as a function of the activity in the image sequence.

Although phototoxicity reduction in retinal surgery provided the motivating focus for this experiment, our technical approach to the problem is potentially more broadly applicable. We have developed methods for actively controlling the illumination spectrum in video microscopy and endoscopy and for fusing the resulting image sequences to form continuous and coherent image sequences. These methods are applicable in many clinical applications, including neurosurgery and cancer surgery. For example, changing the illumination spectrum can be used to improve tissue contrast or discrimination or the depth of penetration of light into tissue structures. The methods proposed in this paper may be adapted to such cases while still giving the surgeon more options on the actual visualization.

Phototoxicity Reduction Technique #3: Color Companding of Phototoxic Wavelengths The final technique of these examples for reducing phototoxicity is to perform companding of color information that corresponds to highly phototoxic wavelengths within the illumination spectrum. This is done by reducing the intensity of highly phototoxic wavelengths to some fractional value while keeping the wavelengths of low phototoxicity at normal intensity. The result is an image with weakened color information at colors corresponding to the attenuated wavelengths. Using a color boost model, this weakened color information is restored to normal levels by computationally boosting the color response of the affected wavelengths by an amount proportional to the magnitude of attenuation.

The trade-off for this approach is that the granularity of the boosted color information is less precise, which results in increasingly large step sizes in color value as the boost magnitude increases. The increased step sizes only affect the color channels being boosted, however. For example, if blue light emission is reduced and the blue image color correspondingly boosted by a factor of two, the step size in blue pixel values will increase from one to two, while the step size in red and green pixel values will remain, for the most part, unaffected with a value of one. The gain in phototoxicity reduction by this technique can be dramatic. With this technique, images can be captured under an illumination spectrum comprised of an intensity gradient that is weighted according to the phototoxicity of each constituent wavelength. Wavelengths of low phototoxicity can illuminate at high intensity, providing fine-granularity color information, while wavelengths of high phototoxicity illuminate at diminished intensity, providing large-granularity color information after boosting. Using low boost values, such as two, provide almost unnoticeable effect on image quality while offering potentially drastic reduction in phototoxicity.

A simple linear model that maps the illumination intensity of each LED channel to its corresponding camera response in RGB pixel value is one possible approach. This model assumes a linear camera response, i.e. doubling the intensity of an LED channel corresponds to doubling the pixel value response in the captured image. At the time this model was developed for this example, only red, green, and blue LEDs were used for illumination (the yellow channel had not yet been added).

The color boost model is represented by equation (2). X is a 3×1 vector containing the illumination intensity (range [0,1]) of each LED channel. In this case, three LED channels have colors red, green, and blue. C is a 3×1 vector representing a color-boosted RGB pixel value in the video image (range [0,255]). K is a 3×3 matrix mapping illumination intensity of each LED channel to its corresponding camera response in pixel value. λ is a 3×3 diagonal matrix containing the boost parameter for each LED channel. Under normal, non-boosting conditions, λ is the identity matrix. Equation (3) shows the same equation, but with each element expanded into its constituent sub-elements.

$$C = K\lambda X \quad (2)$$

$$\begin{bmatrix} C_R \\ C_G \\ C_B \end{bmatrix} = \begin{bmatrix} K_{R,R} & K_{G,R} & K_{B,R} \\ K_{R,G} & K_{G,G} & K_{B,G} \\ K_{R,B} & K_{G,B} & K_{B,B} \end{bmatrix} \begin{bmatrix} \lambda_R & 0 & 0 \\ 0 & \lambda_G & 0 \\ 0 & 0 & \lambda_B \end{bmatrix} \begin{bmatrix} X_R \\ X_G \\ X_B \end{bmatrix} \quad (3)$$

The K matrix is camera-dependent and is determined experimentally in a calibration step. This calibration is done by illuminating a white sheet with one LED channel at a time set to maximum brightness. The average pixel value from the camera image becomes the camera response for that LED channel. For example, when the red LED channel is illuminated, the camera response is $[219, 7, 0]^T$ in terms of RGB values. This vector comprises the first column of matrix K. Similarly, the camera response to the green and blue channels form the remaining columns of matrix K. The complete calibration matrix K for the ACULED VHL LED light source with red, green, and blue LEDs and the Flea2 Point Grey Research cameras used in one embodiment of our system is shown in equation (4) below:

$$K = \begin{bmatrix} 219 & 2 & 1 \\ 7 & 136 & 76 \\ 0 & 26 & 184 \end{bmatrix}. \quad (4)$$

As an example scenario using this phototoxicity reduction technique, consider the case of reducing the blue LED intensity to 50%. In order to maintain the same apparent color balance in the video image, the boost value $\lambda_B$ for the blue LED is set to two. However, the model we have from equation (2) is not yet in the needed form to compute the color boost. C is the value we wish to calculate for each pixel; K and λ are known. What remains is to determine X for each pixel. However, the raw pixel values from a captured video image do not provide X; rather, these pixel values correspond to the value that C would be given no color boost (call this value $C_{REAL}$). This makes intuitive sense because the color boost is a computational step following image capture. At the point of image capture, the image represents the real pixel values which intuitively have no applied color boost. What we must do is determine X from our model based on the assumption that the $C_{REAL}$ we are given has no boost factor, i.e. assuming λ is the identity matrix. Then we can plug this X into our boosting model and calculate a new C with the desired boost parameters applied.

According to the model in equation (2), λX is equivalent to K inverse applied to C. For the pixel values in the raw image, we know λ is identity and C is also known as $C_{REAL}$, the value of each pixel in the image. Thus, we have that X is equal to the value shown in equation (5). Because we know K and we know $C_{REAL}$, we now know X for our boost model.

$$X = K^{-1} C_{REAL} \quad (5)$$

Substituting equation (5) for X in the boost model leads to equation (6) for calculating a new C adjusted according to the boost parameters. This new C becomes the new pixel value in the color-boosted image.

$$C = K\lambda K^{-1} C_{REAL} \quad (6)$$

In implementing this technique, the λ term in the model may be automatically updated based on the LED intensities set by the user. Because the PC application knows the intensity setting for each LED channel, λ can be automatically calculated to achieve consistent color balance in the image. Thus, the user may change the color balance at will, while the algorithm automatically adjusts the boost to maintain uniform color balance. Typically, a user would reduce the blue and green color balance relative to red while observing the resulting image quality as the algorithm attempts to keep the color balance consistent. In this way, the user may reduce the harmful wavelengths to as low a setting as possible while still preserving an image of satisfactory quality.

As an alternative to the scheme provided above, instead of using a color boosting model to recalculate pixel values in the image, the camera's built-in white balance may be adjusted to correct for changes in the relative illumination intensities of different wavelengths. This would require another model to predict the optimal white balance settings dependent on the relative intensities of each color channel.

Phototoxicity Reduction Technique #4: Adaptive Spectrum Imaging

In order to provide the surgeon with accurately colored images when using the light source such as in the example above, we present an algorithm that dynamically chooses which illumination type to use at each time step, depending on estimates of the rendered image quality and phototoxicity levels induced. That is, the quality of the recolorization and phototoxicity levels are continuously monitored, allowing us to estimate when it is appropriate to use white light illumination. In general, this occurs when the scene changes cannot be adequately "predicted" with the current available information.

The system we use includes a device capable of illuminating the retina using either white light, or less phototoxic red light as described above. We define the sequence of images provided by the system as $I=\{I_1, \ldots, I_N\}$ for N discrete time steps. Each image $I_t$ is associated with a particular illumination $L_t$, where $L_t=1$ means that white light was used at time t, and $L_t=0$ means that red light was used. Consequently, when $L_t=1$ all three color channels are available, $I_t=\{I_t^R, I_t^G, I_t^B\}$, whereas when $L_t=0$ only the red channel $I_t^R$ is available. We define the illumination history as $L_t=\{L_1, \ldots, L_t\}$. As in the example above, the overall rate at which white light is defined as in equation (1). We denote by $F_t$ the final fully colored image rendered by our algorithm. To recolor the monochromatic images we maintain a color model of the scene for each time t, $M_t=\{M_t^R, M_t^G, M_t^B\}$.

Our goal then is to choose which illumination type, $L_{t+1}$, to use for the next time step. To do this, our criterion is to maximize a quantitative estimate of the patient's wellbeing. This criterion combines the two costs incurred by the patient at time t: the "surgeon impairment cost" and the "phototoxicity cost". The surgeon impairment cost, $S(\epsilon_t)$, is the cost of being accidentally harmed by the surgeon because of the error levels present in the recolored images, $\epsilon_t$. The phototoxicity cost, $T(L_t)$, is given by the damage to the patient produced by the illumination. In the next section we describe these costs in more detail. In the section after that, we show how these costs are combined to select which illumination type to use at each time step Modeling the Cost Functions As described in the previous section, there are two different costs incurred by the patient at time t during the procedure. The first cost is the "surgeon impairment cost", $S(\epsilon_t)$. This is the cost (for the patient) of being accidentally harmed by the surgeon at time t. Clearly this risk (and hence the cost) increases as the recolorization error, $\epsilon_t$ (defined below) increases, since the surgeon is relying on poorer images to perform his job. The exact relationship between this cost and the error is unknown and depends, among many things, on the particular surgeon using the system. However we expect $S(\epsilon)$ to be an increasing function that levels off at a certain error, $\epsilon^*$, at which stage the quality of the image is so poor that further deterioration does not result in additional risk. In practice, we will make sure that the system remains in the linear part of S, far from the critical value $\epsilon^*$, where the surgeon is critically impaired. Based results from the examples above, we will model this relationship with the following function, $$S(\epsilon) = \begin{cases} 1 & \text{if } \epsilon > \epsilon^* \\ \frac{\epsilon}{\epsilon^*} & \text{otherwise} \end{cases} \quad (1.1)$$

The recolorization error, $\epsilon$, is due to the fact that the color model at any given time is not perfect, since the background scene changes due to the manipulations performed by the surgeon. In order to compute this error, we note that errors are only committed in the green and blue channels, since the red channel is observed at all times. We assume that the error committed in the green and blue channels at time t, $\epsilon^{G,B}_t$, is approximately equal to the error that would be obtained in the red channel, $\epsilon^R_t$, if it were treated as the green and blue channels ($\epsilon^{G,B}_t \approx \epsilon^R_t$). Since the red channel is available at all times irrespective of the illumination type, $\epsilon^R_t$ can be directly computed as, $$\epsilon^R_t = \|M_t^R - M_{t_w}^R\|_2 \quad (1.2)$$

where $t_w$ is the last time step in which $L_{tW}=1$. Assuming further that the error does not change significantly in one time step, we approximate the error at time t+1 by the error at time t, hence $\epsilon^{\hat{}G,B}_{t+1} \approx \epsilon^{\hat{}G,B}_t \approx \epsilon^R_t$.

The second cost, the "phototoxicity cost," $T(L_t)$, is the estimated damage at time t suffered by the patient because of the illumination used up to this point in time $L_t$. It seems reasonable from the current literature (Ham, W. J., Mueller, H., Ru olo, J. J., Guerry, D., Guerry, R.: Action spectrum for retinal injury from near-ultraviolet radiation in the aphakic monkey. Am J Ophthalmol 93 (1982) 299-306) to relate the amount of phototoxic damage, T, to a function of the recent light exposure $\phi(L_t)$, where $\phi(L_t)$ is a function that models how the illumination history $L_t$ affects a cell at time t. We chose to define $\phi(L_t)$ as an exponential loss (approximated from Ham et al., ibid). That is, as time goes on, the influence of the past decreases exponentially fast. Hence, we approximate the phototoxicity cost by, $$T(L_t) = \begin{cases} 1 & \text{if } \varphi(L_t) > L^* \\ e^{\frac{-(\varphi(L_t)-L^*)^2}{2}} & \text{otherwise} \end{cases} \quad (1.3)$$

where $L^*$ is some level of illumination at which irreversible damage to the patient (cell death) is produced.

It must be noted that while the choice of these functions is based on reasonable assumptions, these functions ultimately need to be empirically determined.

Choosing the Next Illumination Type

We can then formally define the estimated total cost for the patient at time t+1 as the sum of the two costs described in the previous section, $$E(L_{t+1}, \epsilon^{\hat{}}_{t+1}) = (1-\lambda)S(\epsilon^{\hat{}}_{t+1}) + \lambda T(L_{t+1}). \quad (1.4)$$

where, $\epsilon^{\hat{}}_{t+1}$, is the measure of the recolorization error defined in Eq. 1.2, $L_{t+1}$ is the history of illuminations at time (t+1) and $\lambda$ is a tuning parameter which can be adjusted by the user (i.e. surgeon) to specify a bias for either image quality or phototoxicity. We select the next illumination type, by minimizing the patient wellbeing cost, $$L_{t+1} = \arg\min_L E(L_{t+1}, \epsilon^{\hat{}}_{t+1}) = \arg\min_L \{(1-\lambda)S(\epsilon^{\hat{}}_{t+1}) + \lambda T(L_{t+1})\}. \quad (1.5)$$

Notice that L can take only two values (0 or 1). Hence, this optimization reduces to $$(1-\lambda)S(\epsilon^{\hat{}}_{t+1}) + \lambda(T([L_t;1]) - T([L_t;0])) \geq 0 \quad (1.6)$$

Since $\epsilon^{\hat{}}_{t+1} = 0$ when $L_{t+1}=1$, and $\epsilon^{\hat{}}_{t+1} \approx \epsilon^{\hat{}}_t$ when $L_{t+1}=0$, all the quantities in Eq. 1.6 are known and choosing the next illumination type simply reduces to determining whether or not Eq. 1.6 is true.

Adaptive Active Scene Rendering

Figure 10:
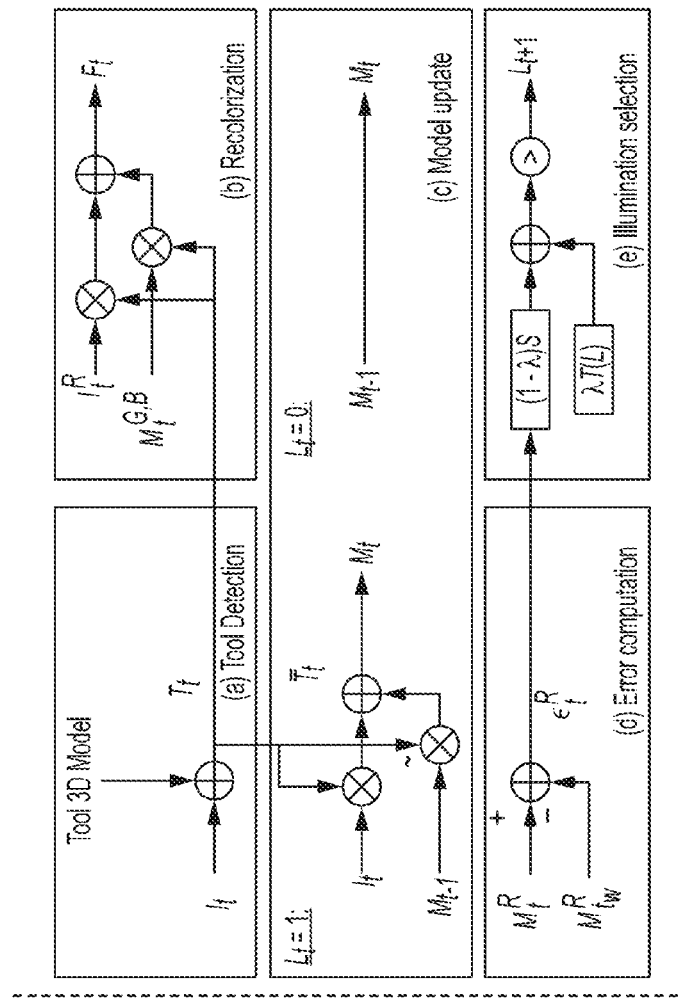
FIG. 10 provides a block diagram of the system according to an embodiment of the current invention.
Figure 9:
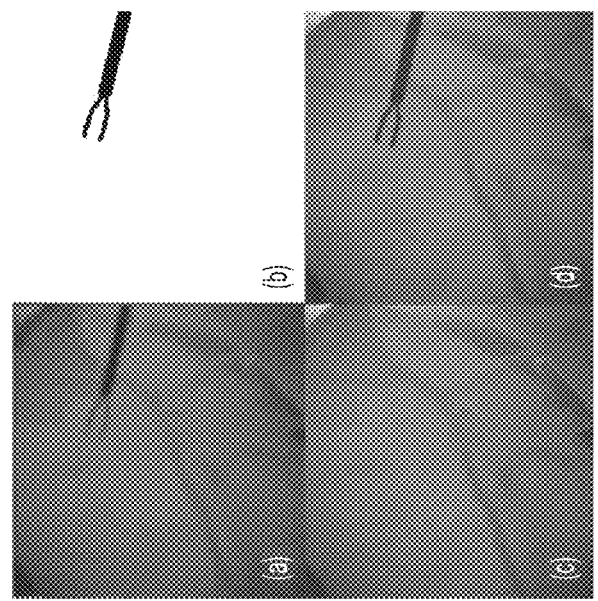
FIG. 9 shows intermediate steps using the AASR algorithm: (a) non-white image provided by the device when $L_t=0$, (b) tool segmentation, (c) representation of $M_t$ and (d) recolored image by AASR.

We now present the outline of our algorithm according to an embodiment of the current invention: Adaptive Active Scene Rendering (AASR). FIGS. 9 and 10 provide a visual outline of AASR and associated images. First for each image $I_t$, (FIGS. 9(a) and 10(a)) we detect and segment the tool in the image by using a 3D tool model (see example above for more details). This provides us with a mask region for the tool, $T_t$ (FIG. 9(b)). Then, in order to compute the new color model: if $L_t=1$, $M_t$ is computed by keeping pixel regions of $M_{t-1}$ which appear where the tool is located and using $I_t$ for regions where the tool is not present (FIG. 10(c)). This is done by using $T_t$ to mask regions of the tool and allows for regions displaying the retina to be updated, keeping tool regions unchanged (similar to the work in Sznitman, R., Lin, H., Manaswi, G., Hager, G.: Active background modeling: Actors on a stage. ICCV, Workshop on Visual Surveillance (2009) 1222-1228). If $L_t=0$, then $M_t=M_{t-1}$ (FIG. 9(c)). Rendering the recolored image, $F_t$, is then done by combining $M^{G,B}_t$ and $I^R_t$ on regions outside the tool, and using a tool color model to fill in the tool ((FIGS. 10(b)) and 9(d)). Having computed these, we can then estimate the error, $\epsilon_t$, using $M^R_t$ and $M^R_{t,w}$, as described by Eq. 1.2 (FIG. 10(d)), and choosing the following illumination type can be computed as in Eq. 1.6 (FIG. 10(e)).

Experiments

We now show how our system performs on image sequences from phantoms and from chorioallatonic chicken embryos. First, a quantitative comparison of AASR and a state-of-the-art method is presented; where it is shown that AASR surpasses ASR in a setting where ground truth is known. This is shown by measuring both image recoloring quality and quantity of white light used. We then show qualitative results of our algorithm on image sequences.

To validate the approach described above, we recorded 5 image sequences of membrane peelings on phantom eyes using only white light. Each sequence consists of approximately 300 frames in similar visual settings. Doing so allows us to synthetically generate limited-spectrum images at any given time, by using only the red channel of white light images. This provides us with a way to quantitatively compare AASR and ASR, as ground truth is available.

For each image sequence we then ran AASR with three different settings: $\lambda=\{0.25, 0.5, 0.75\}$. This allows us to see results for cases where the surgeon applies a bias towards image quality, phototoxic levels, or no bias at all. For each image sequence, we also generated 4 recolored sequences using ASR, with different values of $\phi=\{½, ¼, ⅛, 1/16\}$. As in the example above, the $L_2$ (or mean squared error) norm is chosen to measure the error between the ground truth and the rendered images. In order to estimate phototoxicity levels, we observe the proportion of white-light images used.

In FIG. 11A we show the results of this experiment by plotting the average recolorization error against the average estimated phototoxicity level. The dotted line (4 vertices; 1 for each value of $\phi$) shows how ASR performs while the full line describes the performance of AASR (3 vertices; 1 for each value of $\lambda$). In general, we can notice that both methods displays a trade-off in accuracy: reducing one type of error induces the other and vice versa. We can also see that the AASR curve lies below that of ASR for every recolorization error level, hence achieving smaller total costs for the patient. In general, from our current experimental setup, AASR significantly outperform ASR, for the values of $\lambda$ specified. Also, note that if all incoming images were registered to a reference frame (as in the example above) an additional reduction in colorization error would be expected.

Having observed that AASR provides a better way to model retinal-type scenes, we now present results on a typical image sequence of a chorioallatonic membrane peel from a 12 day old chicken embryo. In FIG. 11B we show a small set of images from this sequence and the resulting recolorization using AASR ($\lambda=0.5$). The original and recolored video sequence can be seen in a video included in the supplementary materials. In the video, the same peeling sequence is visible and each row corresponds to a different value for $\lambda=\{0.25, 0.5, 0.75\}$. The first column shows the original images. The second column displays the images provided by the device, while the third column shows the images recolored by AASR. The last column displays the retina color model over time. Other similar video sequences are provided in the supplementary materials.

Notice that in general, in image sequences which contain little membrane manipulations, few white light images are used. Since in this scenario our prediction model is capable of correctly estimating the colors of the retina, few white light images are necessary. Conversely, frames which show membrane peeling require more frequent white light illumination, in order to correctly render the colors. This indicates that the framework is able to choose which illumination type to use depending on the surgeon's actions.

In this example we have presented a novel algorithm that can be used to reduce toxic light exposure during retinal microsurgery. When used with the LED light source according to some embodiments of the current invention, our recoloring scheme can dynamically choose the illumination based on the circumstances, reducing potential light induced retinal toxicity. Our algorithm balances the risks of phototoxic retinal damage with the illumination requirements of the operating surgeon to perform the surgical tasks. In this example we provide qualitative and quantitative evidence that this novel method reduces the dose of light, and hence retinal damage, while maintaining sufficient illumination to execute required surgical maneuvers safely.

While the results we have presented are in part dependent on the modeling choices of the cost functions, our framework is generic enough to accommodate a large number of functions. This being said, a natural future direction to im-prove the present work is to empirically determine the specific forms of the cost functions to use. Determination of these relationships would permit a truthful quantitative evaluation of the harm reduction. In ongoing and future work, we will be exploring these issues.

When used individually, any of these phototoxicity reduction techniques can easily reduce exposure of the most hazardous white light wavelengths by at least 50%. When used in parallel, truly drastic reduction in white light exposure is possible. As a typical example, suppose we have a video frame rate of 30 Hz and a typical camera shutter time of 16.5 milliseconds. Applying camera shutter synchronization reduces all light exposure to 50%. Setting the dark light interval to one reduces exposure to white light by another 50% down to 25% of the original. With a dark light interval equal to one, color mapping is very accurate and thus has little effect on video quality. Next, apply color companding by reducing the blue LED intensity to 50% and applying a $\lambda_B$ boost value of 2. This reduces blue light exposure by another 50%, totaling 12.5% of the original blue light intensity. Applying a factor two color boost to the blue light response also has largely negligible impact on image quality, since the blue pixel value step size changes from 1 to only 2, dividing the value range [0,255] into 128 possible values rather than 256. Meanwhile, color rendition for red and green color spectrums remain the same. The resulting impact on image quality may not even be noticeable by the average user. In the end, blue light is reduced to 12.5%, green light to 25%, and red light to 50% of the original white light intensity. Because phototoxicity primarily occurs within the blue wavelength range, the resulting light spectrum provides drastically safer illumination compared with no phototoxicity reduction. Further, by processing the images, the computer may adaptively adjust the multiplexing rate and/or the relative intensity of phototoxic illumination in color toxicity to provide only the minimum amount of phototoxic illumination needed at any particular time in the procedure. Similarly, the surgeon may be provided with an explicit command method such as a foot pedal or voice recognition system to explicitly adjust the parameters of the various phototoxicity reduction methods or to select different modes of operation of the system.

We have developed an illumination system that can be used for retinal surgery that drastically reduces exposure to highly phototoxic wavelengths inherent to white light illumination. The illumination system carries the potential to significantly impact retinal surgery outcomes by ridding many complications that result when the retina is damaged by intense illumination during surgery. Since video monitoring is used for viewing the surgical field when phototoxicity reduction methods are enabled, a change to the way retinal surgery is currently performed may result. Instead of viewing the procedure through an optical microscope, surgeons would use a video-based display. Using video-based visualization for eye surgery may well become the preferred method of the future, as it can provide many benefits to the surgeon, including improved ergonomics and less physical fatigue resulting from back and neck strain following long hours working at the microscope. In addition, the added potential to integrate information sources into the surgeon's field-of-view is a further motivating factor towards video-based surgery. Such information may include sources such as sophisticated navigation and sensing aids, as well as preoperative imaging data, such as fundus images.

A secondary benefit of the illumination system can include the ability to tune the color temperature to not only reduce phototoxicity, but also to improve visualization when a certain color temperature provides better rendition of an object of interest. A further possible use of the illumination system can be to add special-purpose illumination channels, such as a channel that activates a fluorescent dye. The excitation phase could be performed while the camera shutter is closed, so as not to alter the light spectrum used for visualization, for example. IR light could also be used for very low phototoxicity illumination or to see deep into retinal tissue.

As a modification to the system described, the light source could be altered to work with light sources other than LEDs, including Xenon light sources which are the medical standard. This modification would not allow for a tunable color temperature, but the light output could still be shuttered to correspond with the shutter and frame times of the camera. A low phototoxicity spectrum could also be used in this scenario, either by rapid switching to an alternative light source or through the use of dynamically interchangeable filters. Shuttering a Xenon light source in this way could use a mechanical-based shutter design rather than the electronic-based approach taken with the LED light source.

The embodiments illustrated and discussed in this specification are intended only to teach those skilled in the art the best way known to the inventors to make and use the invention. Figures are not drawn to scale. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An observation system for viewing light-sensitive tissue, comprising:
    an illumination system;
    an imaging system arranged to be in an optical path of light from said light-sensitive tissue upon being illuminated by said illumination system, said imaging system comprising an optical detector and a data processing system; and
    an image display system in communication with said imaging system to display an image of said portion of said light-sensitive tissue,
    wherein said illumination system comprises a light source and a light source controller constructed and arranged to control at least one of a spectral composition and intensity of light that illuminates said light-sensitive tissue,
    wherein said imaging system is configured to image at least a portion of said light-sensitive tissue upon being illuminated by said illumination system;
    wherein said illumination system is configured to illuminate said light-sensitive tissue with a reduced amount of light within a preselected wavelength range compared to substantially white light illumination,
    wherein said light source controller causes said light source to illuminate said light-sensitive tissue with substantially white light for a first period of time and with light that is non-toxic to said light-sensitive tissue for a second period of time thus providing said reduced amount of light within said preselected wavelength range,
    wherein said light source controller communicates with said imaging system such that said optical detector acquires imaging data during said first period of time and during said second period of time,
    wherein said data processing system uses said imaging data acquired during said first period of time to compensate said imaging data acquired over said second period of time such that said image displayed by said image display system appears more like an uninterrupted white-light-illuminated image, and
    wherein said image of said portion of said light-sensitive tissue is a full color image.

2. An observation system according to claim 1, wherein said light source comprises a plurality of light-emitting diodes and said light source controller is adapted to turn said light-emitting diodes on and off.

3. An observation system according to claim 2, wherein said plurality of light-emitting diodes comprises at least one light-emitting diode for emitting light in each of three primary color regions of a spectrum of said substantially white light.

4. An observation system according to claim 2, wherein said plurality of light-emitting diodes comprises a red, a green, a yellow and a blue LED.

5. An observation system according to claim 2, wherein said plurality of light-emitting diodes comprises an infrared LED.

6. An observation system according to claim 2, wherein said imaging system comprises a plurality of optical detection elements, each having a spectral sensitivity that substantially matches a spectral emission of a corresponding one of said plurality of light-emitting diodes.

7. An observation system according to claim 1, wherein said light that is non-toxic to said light-sensitive tissue is substantially free of blue and shorter wavelength light.

8. An observation system according to claim 1, wherein said light that is non-toxic to said light-sensitive tissue is red or infrared light.

9. An observation system according to claim 1, wherein said light source comprises a plurality of light-emitting diodes and said light source controller is adapted to turn said light-emitting diodes on and off to selectively provide said substantially white light and said light that is non-toxic to said light-sensitive tissue.

10. An observation system according to claim 1, wherein said data processing system segments at least one of background image portions or images of tools within said image from said light-sensitive tissue.

11. An observation system according to claim 1, wherein said data processing system is adapted to apply a color boost model to compensate for said reduced amount of light within said preselected wavelength range.

12. An observation system according to claim 11, wherein said color boost model includes companding.

13. An observation system according to claim 1, wherein said data processor compensates said imaging data acquired over said second period of time by at least one of multiplexed spectrum imaging, color companding, adaptive multispectral imaging or any combination thereof.

14. An observation system according to claim 1, wherein said image of said portion of said light-sensitive tissue includes color information provided by said substantially white light illumination.

15. A method of displaying an image of light-sensitive tissue, comprising:
    illuminating said light-sensitive tissue with multispectral light for a first period of time;
    imaging said light-sensitive tissue over said first period of time upon being illuminated with said multispectral light; and
    displaying said image of said light-sensitive tissue for a second period of time that is longer than said first period of time,
    wherein said second period of time includes a period of time in which said light-sensitive tissue is free of said multispectral illumination, and
    wherein said imaging said light-sensitive tissue includes compensating for said period of time in which said light-sensitive tissue is free of said multispectral illumination to approximate an image of said light-sensitive tissue as it would appear had it been under said multispectral illumination for said entire second period of time.

* * * * *